(12) United States Patent
Shiroff et al.

(10) Patent No.: US 10,327,810 B2
(45) Date of Patent: Jun. 25, 2019

(54) SYSTEMS AND METHODS FOR ENHANCED IMPLANTATION OF ELECTRODE LEADS BETWEEN TISSUE LAYERS

(71) Applicant: Mainstay Medical Limited, Swords, County Dublin (IE)

(72) Inventors: Jason Alan Shiroff, Edina, MN (US); Henry Demorett, Prior Lake, MN (US); John Beck, Ramsey, MN (US); Sidney Hauschild, Cottage Grove, MN (US)

(73) Assignee: Mainstay Medical Limited, Swords, County Dublin (IE)

( * ) Notice: Subject to any disclaimer, the term of this patent is extended or adjusted under 35 U.S.C. 154(b) by 322 days.

(21) Appl. No.: 15/202,485

(22) Filed: Jul. 5, 2016

(65) Prior Publication Data
US 2018/0008311 A1 Jan. 11, 2018

(51) Int. Cl.
*A61B 17/34* (2006.01)
*A61N 1/05* (2006.01)
*A61B 18/00* (2006.01)

(52) U.S. Cl.
CPC .......... *A61B 17/3468* (2013.01); *A61B 18/00* (2013.01); *A61N 1/0551* (2013.01); *A61N 1/0558* (2013.01); *A61B 2018/00339* (2013.01)

(58) Field of Classification Search
CPC .............. A61N 1/36071; A61N 1/0551; A61N 1/36017; A61N 1/0558; A61B 17/3468; A61B 18/00; A61B 2018/00339
USPC ........................................................ 606/129
See application file for complete search history.

(56) References Cited

U.S. PATENT DOCUMENTS

| 3,077,884 A | 2/1963 | Batrow et al. |
| 3,416,534 A | 12/1968 | Quinn |
| 3,710,777 A | 1/1973 | Sparks |
| 3,754,555 A | 8/1973 | Schmitt |
| 3,875,947 A | 4/1975 | Jula et al. |
| 3,893,463 A | 7/1975 | Williams |
| 3,902,501 A | 9/1975 | Citron et al. |
| 3,976,082 A | 8/1976 | Schmitt |
| 3,999,551 A | 12/1976 | Spitz et al. |

(Continued)

FOREIGN PATENT DOCUMENTS

| CN | 1211930 C | 7/2005 |
| CN | 101678203 | 3/2010 |

(Continued)

OTHER PUBLICATIONS

Deckers, et al., Chronic Low Back Pain: Restoration of Dynamic Stability, Neuromodulation, 18:478-486 (2015).

(Continued)

*Primary Examiner* — Kathleen S Holwerda
(74) *Attorney, Agent, or Firm* — Foley & Lardner LLP; Christopher C. Bolten; Nicola A. Pisano

(57) ABSTRACT

Systems and methods for enhanced implantation of an electrode lead for neuromuscular electrical stimulation of tissue associated with control of the lumbar spine for treatment of back pain, in a midline-to-lateral manner are provided. The implanted lead may be secured within the patient and used to restore muscle function of local segmental muscles associated with the lumbar spine stabilization system without disruption of the electrode lead post-implantation due to anatomical structures.

30 Claims, 14 Drawing Sheets

(56) References Cited

U.S. PATENT DOCUMENTS

| | | |
|---|---|---|
| 4,010,757 A | 3/1977 | Jula et al. |
| 4,026,301 A | 5/1977 | Friedman et al. |
| 4,031,899 A | 6/1977 | Renirie |
| 4,149,528 A | 4/1979 | Murphy |
| 4,235,246 A | 11/1980 | Weiss |
| 4,269,198 A | 5/1981 | Stokes |
| 4,342,317 A | 8/1982 | Axelgaard |
| 4,408,609 A | 10/1983 | Axelgaard |
| 4,418,693 A | 12/1983 | Leveen et al. |
| 4,528,984 A | 7/1985 | Morawetz et al. |
| 4,549,556 A | 10/1985 | Tarjan et al. |
| 4,574,806 A | 3/1986 | McCarthy |
| 4,658,835 A | 4/1987 | Pohndorf |
| 4,832,687 A | 5/1989 | Smith |
| 4,917,093 A | 4/1990 | Dufresne et al. |
| 5,069,680 A | 12/1991 | Grandjean |
| 5,199,430 A | 4/1993 | Fang et al. |
| 5,215,088 A | 6/1993 | Normann et al. |
| 5,300,108 A | 4/1994 | Rebell et al. |
| 5,330,515 A | 7/1994 | Rutecki et al. |
| 5,376,108 A | 12/1994 | Collins et al. |
| 5,496,345 A | 3/1996 | Kieturakis et al. |
| 5,501,452 A | 3/1996 | Halvorson |
| 5,507,788 A | 4/1996 | Lieber |
| 5,522,854 A | 6/1996 | Ideker et al. |
| 5,569,183 A | 10/1996 | Kieturakis |
| 5,638,825 A | 6/1997 | Yamazaki et al. |
| 5,733,307 A | 3/1998 | Dinsdale |
| 5,741,321 A | 4/1998 | Brennen |
| 5,782,841 A | 7/1998 | Ritz et al. |
| 5,807,234 A | 9/1998 | Bui et al. |
| 5,873,900 A | 2/1999 | Maurer et al. |
| 5,916,172 A | 6/1999 | Hodges et al. |
| 5,957,968 A | 9/1999 | Belden et al. |
| 6,104,957 A | 8/2000 | Alo et al. |
| 6,119,516 A | 9/2000 | Hock |
| 6,314,325 B1 | 11/2001 | Fitz |
| 6,319,241 B1 | 11/2001 | King et al. |
| 6,324,414 B1 | 11/2001 | Gibbons et al. |
| 6,366,819 B1 | 4/2002 | Stokes |
| 6,381,496 B1 | 4/2002 | Meadows et al. |
| 6,406,421 B1 | 6/2002 | Grandjean et al. |
| 6,473,654 B1 | 10/2002 | Chinn |
| 6,516,227 B1 | 2/2003 | Meadows et al. |
| 6,527,787 B1 | 3/2003 | Fogarty et al. |
| 6,565,594 B1 | 5/2003 | Herweck et al. |
| 6,600,954 B2 | 7/2003 | Cohen et al. |
| 6,600,956 B2 | 7/2003 | Maschino et al. |
| 6,605,094 B1 | 8/2003 | Mann et al. |
| 6,671,557 B1 | 12/2003 | Gliner |
| 6,735,474 B1 | 5/2004 | Loeb et al. |
| 6,839,594 B2 | 1/2005 | Cohen et al. |
| 6,845,271 B2 | 1/2005 | Fang et al. |
| 6,862,479 B1 | 3/2005 | Whitehurst et al. |
| 7,018,384 B2 | 3/2006 | Skakoon |
| 7,096,070 B1 | 8/2006 | Jenkins et al. |
| 7,206,641 B2 | 4/2007 | Ignagni et al. |
| 7,218,970 B2 | 5/2007 | Ley et al. |
| 7,239,918 B2 | 7/2007 | Strother et al. |
| 7,286,879 B2 | 10/2007 | Wallace |
| 7,317,948 B1 | 1/2008 | King et al. |
| 7,324,852 B2 | 1/2008 | Barolat et al. |
| 7,324,853 B2 | 1/2008 | Ayal et al. |
| 7,337,005 B2 | 2/2008 | Kim et al. |
| 7,337,006 B2 | 2/2008 | Kim et al. |
| 7,369,894 B2 | 5/2008 | Gerber |
| 7,389,149 B2 | 6/2008 | Rossing et al. |
| 7,444,181 B2 | 10/2008 | Shi et al. |
| 7,447,546 B2 | 11/2008 | Kim et al. |
| 7,450,993 B2 | 11/2008 | Kim et al. |
| 7,489,561 B2 | 2/2009 | Armstrong et al. |
| 7,493,175 B2 | 2/2009 | Cates et al. |
| 7,499,746 B2 | 3/2009 | Buhlmann et al. |
| 7,502,651 B2 | 3/2009 | Kim et al. |
| 7,515,971 B1 | 4/2009 | Doan |
| 7,580,753 B2 | 8/2009 | Kim et al. |
| 7,668,598 B2 | 2/2010 | Herregraven et al. |
| 7,684,866 B2 | 3/2010 | Fowler et al. |
| 7,708,763 B2 | 5/2010 | Selover et al. |
| 7,761,166 B2 | 7/2010 | Giftakis et al. |
| 7,792,591 B2 | 9/2010 | Rooney et al. |
| 7,797,053 B2 | 9/2010 | Atkinson et al. |
| 7,813,803 B2 | 10/2010 | Heruth et al. |
| 7,908,015 B2 | 3/2011 | Lazeroms et al. |
| 7,917,230 B2 | 3/2011 | Bly |
| 7,930,039 B2 | 4/2011 | Olson |
| 7,981,144 B2 | 7/2011 | Geist et al. |
| 8,016,846 B2 | 9/2011 | McFarlin et al. |
| 8,065,020 B2 | 11/2011 | Ley et al. |
| 8,082,039 B2 | 12/2011 | Kim et al. |
| 8,170,690 B2 | 5/2012 | Morgan et al. |
| 8,229,565 B2 | 7/2012 | Kim et al. |
| 8,229,656 B2 | 7/2012 | Ikushima et al. |
| 8,249,701 B2 | 8/2012 | Imran et al. |
| 8,249,713 B2 | 8/2012 | Fang et al. |
| 8,380,318 B2 | 2/2013 | Kishawi et al. |
| 8,391,966 B2 | 3/2013 | Luo et al. |
| 8,409,233 B1 | 4/2013 | Chinn et al. |
| 8,428,728 B2 | 4/2013 | Sachs |
| 8,498,697 B2 | 7/2013 | Yong et al. |
| 8,606,358 B2 | 12/2013 | Sachs |
| 8,798,005 B1 | 8/2014 | Vargantwar et al. |
| 8,886,337 B2 | 11/2014 | Bennett et al. |
| 8,965,516 B2 | 2/2015 | Bennett et al. |
| 9,072,897 B2 | 7/2015 | Sachs et al. |
| 9,079,019 B2 | 7/2015 | Crosby et al. |
| 9,108,053 B2 | 8/2015 | Crosby et al. |
| 9,320,847 B2 | 4/2016 | Rooney et al. |
| 9,861,811 B2 | 1/2018 | Crosby et al. |
| 2001/0053885 A1 | 12/2001 | Gielen et al. |
| 2002/0065543 A1 | 5/2002 | Gomperz et al. |
| 2002/0099419 A1 | 7/2002 | Cohen et al. |
| 2002/0115945 A1 | 8/2002 | Herman et al. |
| 2002/0147485 A1* | 10/2002 | Mamo ............... A61N 1/0551 607/116 |
| 2002/0156513 A1 | 10/2002 | Borkan |
| 2002/0161415 A1 | 10/2002 | Cohen et al. |
| 2002/0183765 A1 | 12/2002 | Adams |
| 2003/0100933 A1 | 5/2003 | Ayal et al. |
| 2003/0120328 A1 | 6/2003 | Jenkins et al. |
| 2003/0199938 A1 | 10/2003 | Smits et al. |
| 2004/0030360 A1 | 2/2004 | Eini et al. |
| 2004/0097986 A1 | 5/2004 | Adams |
| 2004/0111118 A1 | 6/2004 | Hill et al. |
| 2004/0122482 A1 | 6/2004 | Tung et al. |
| 2004/0147969 A1 | 7/2004 | Mann et al. |
| 2004/0167580 A1 | 8/2004 | Mann et al. |
| 2004/0214790 A1 | 10/2004 | Borgens |
| 2004/0230281 A1 | 11/2004 | Heil et al. |
| 2004/0236383 A1 | 11/2004 | Yelizarov |
| 2005/0070971 A1 | 3/2005 | Fowler et al. |
| 2005/0080472 A1 | 4/2005 | Atkinson et al. |
| 2005/0119713 A1 | 6/2005 | Whitehurst et al. |
| 2005/0149154 A1 | 7/2005 | Cohen et al. |
| 2005/0154389 A1 | 7/2005 | Selover et al. |
| 2005/0165456 A1 | 7/2005 | Mann et al. |
| 2005/0177211 A1 | 8/2005 | Leung et al. |
| 2005/0240243 A1 | 10/2005 | Barolat et al. |
| 2005/0246006 A1 | 11/2005 | Daniels |
| 2005/0283204 A1 | 12/2005 | Buhlmann et al. |
| 2006/0009810 A1 | 1/2006 | Mann et al. |
| 2006/0009827 A1 | 1/2006 | Kurth et al. |
| 2006/0032657 A1 | 2/2006 | Zarembo |
| 2006/0052856 A1 | 3/2006 | Kim et al. |
| 2006/0106416 A1 | 5/2006 | Raymond et al. |
| 2006/0111746 A1 | 5/2006 | Foreman et al. |
| 2006/0111754 A1 | 5/2006 | Rezai et al. |
| 2006/0155341 A1 | 7/2006 | Tehrani et al. |
| 2006/0184222 A1 | 8/2006 | Camps et al. |
| 2006/0206166 A1 | 9/2006 | Weiner |
| 2006/0235484 A1 | 10/2006 | Jaax et al. |
| 2006/0241716 A1 | 10/2006 | Finch et al. |
| 2006/0259074 A1 | 11/2006 | Kelleher et al. |
| 2006/0293662 A1 | 12/2006 | Boyer et al. |

(56) References Cited

U.S. PATENT DOCUMENTS

| | | |
|---|---|---|
| 2007/0027501 A1 | 2/2007 | Jensen et al. |
| 2007/0049980 A1 | 3/2007 | Zielinski et al. |
| 2007/0060967 A1 | 3/2007 | Strother et al. |
| 2007/0073357 A1 | 3/2007 | Rooney et al. |
| 2007/0100377 A1 | 5/2007 | Armstrong et al. |
| 2007/0100391 A1 | 5/2007 | Armstrong |
| 2007/0100408 A1 | 5/2007 | Gerber |
| 2007/0100411 A1 | 5/2007 | Bonde |
| 2007/0123954 A1 | 5/2007 | Gielen et al. |
| 2007/0129780 A1 | 6/2007 | Whitehurst et al. |
| 2007/0135768 A1 | 6/2007 | Carlsen |
| 2007/0179557 A1 | 8/2007 | Maschino et al. |
| 2007/0208392 A1 | 9/2007 | Kuschner et al. |
| 2007/0232936 A1 | 10/2007 | Mann et al. |
| 2008/0026981 A1 | 1/2008 | Muhrer et al. |
| 2008/0103573 A1 | 5/2008 | Gerber |
| 2008/0103579 A1 | 5/2008 | Gerber |
| 2008/0132961 A1 | 6/2008 | Jaax et al. |
| 2008/0167698 A1 | 7/2008 | Kim et al. |
| 2008/0177351 A1 | 7/2008 | Fang et al. |
| 2008/0183221 A1 | 7/2008 | Burdulis |
| 2008/0183257 A1 | 7/2008 | Imran et al. |
| 2008/0200972 A1 | 8/2008 | Rittman et al. |
| 2008/0228241 A1 | 9/2008 | Sachs |
| 2008/0234791 A1 | 9/2008 | Arle et al. |
| 2008/0269716 A1 | 10/2008 | Bonde et al. |
| 2008/0269812 A1 | 10/2008 | Gerber et al. |
| 2009/0005833 A1 | 1/2009 | Cameron et al. |
| 2009/0018576 A1 | 1/2009 | Binmoeller |
| 2009/0105700 A1 | 4/2009 | Anderson |
| 2009/0112263 A1 | 4/2009 | Pool et al. |
| 2009/0192567 A1 | 7/2009 | Armstrong et al. |
| 2009/0210041 A1 | 8/2009 | Kim et al. |
| 2009/0254095 A1 | 10/2009 | Levine et al. |
| 2009/0259280 A1 | 10/2009 | Wilkin et al. |
| 2009/0326613 A1 | 12/2009 | Knoblich |
| 2010/0030227 A1 | 2/2010 | Kast et al. |
| 2010/0036280 A1 | 2/2010 | Ballegaard et al. |
| 2010/0036454 A1 | 2/2010 | Bennett et al. |
| 2010/0082086 A1 | 4/2010 | Zhu |
| 2010/0137938 A1 | 6/2010 | Kishawi et al. |
| 2010/0152808 A1 | 6/2010 | Boggs, II |
| 2010/0152809 A1 | 6/2010 | Boggs, II |
| 2010/0174240 A1 | 7/2010 | Wells et al. |
| 2010/0174326 A1 | 7/2010 | Selover et al. |
| 2010/0179562 A1 | 7/2010 | Linker et al. |
| 2010/0185161 A1 | 7/2010 | Pellegrino et al. |
| 2010/0211149 A1 | 8/2010 | Morgan et al. |
| 2010/0249875 A1 | 9/2010 | Kishawi et al. |
| 2010/0280576 A1 | 11/2010 | Gerber et al. |
| 2010/0292769 A1 | 11/2010 | Brounstein et al. |
| 2011/0004269 A1 | 1/2011 | Strother et al. |
| 2011/0021943 A1 | 1/2011 | Lacour et al. |
| 2011/0022114 A1 | 1/2011 | Navarro |
| 2011/0022123 A1 | 1/2011 | Stancer et al. |
| 2011/0054565 A1 | 3/2011 | Wacnik et al. |
| 2011/0106207 A1 | 5/2011 | Cauller et al. |
| 2011/0160538 A1 | 6/2011 | Ravikumar et al. |
| 2011/0224665 A1 | 9/2011 | Crosby et al. |
| 2011/0224682 A1 | 9/2011 | Westlund et al. |
| 2011/0251662 A1 | 10/2011 | Griswold et al. |
| 2011/0270340 A1 | 11/2011 | Pellegrini et al. |
| 2012/0035953 A1 | 2/2012 | Armstrong |
| 2012/0089153 A1 | 4/2012 | Christopherson et al. |
| 2012/0116477 A1 | 5/2012 | Crowe et al. |
| 2012/0192874 A1 | 8/2012 | Bolea et al. |
| 2012/0215218 A1 | 8/2012 | Lipani |
| 2012/0283800 A1 | 11/2012 | Perryman et al. |
| 2012/0290055 A1 | 11/2012 | Boggs, II |
| 2012/0310140 A1 | 12/2012 | Kramer et al. |
| 2012/0310301 A1 | 12/2012 | Bennett et al. |
| 2012/0310302 A1 | 12/2012 | Bennett et al. |
| 2012/0310314 A1 | 12/2012 | Bennett et al. |
| 2012/0323253 A1 | 12/2012 | Garai et al. |
| 2013/0023974 A1 | 1/2013 | Amrani |
| 2013/0053926 A1 | 2/2013 | Hincapie et al. |
| 2013/0096641 A1 | 4/2013 | Strother et al. |
| 2013/0131766 A1 | 5/2013 | Crosby et al. |
| 2013/0155117 A1 | 6/2013 | Bang |
| 2013/0197607 A1 | 8/2013 | Wilder et al. |
| 2013/0197615 A1 | 8/2013 | Rundle et al. |
| 2013/0211487 A1 | 8/2013 | Fang et al. |
| 2013/0245715 A1 | 9/2013 | Peterson |
| 2013/0261696 A1 | 10/2013 | Thacker et al. |
| 2013/0296966 A1 | 11/2013 | Wongsarnpigoon et al. |
| 2013/0310901 A1 | 11/2013 | Perryman et al. |
| 2013/0338730 A1 | 12/2013 | Shiroff et al. |
| 2014/0031837 A1* | 1/2014 | Perryman .......... A61N 1/36071 606/129 |
| 2014/0046398 A1 | 2/2014 | Sachs et al. |
| 2014/0058476 A1 | 2/2014 | Crosby et al. |
| 2014/0114385 A1 | 4/2014 | Nijhuis et al. |
| 2014/0288616 A1* | 9/2014 | Rawat ................ A61N 1/0551 607/46 |
| 2014/0350653 A1 | 11/2014 | Shiroff et al. |
| 2015/0105840 A1 | 4/2015 | Boggs, II |
| 2016/0045746 A1 | 2/2016 | Jiang et al. |
| 2016/0045747 A1 | 2/2016 | Jiang et al. |
| 2017/0100408 A1 | 4/2017 | Bertolini et al. |

FOREIGN PATENT DOCUMENTS

| | | |
|---|---|---|
| EP | 0 587 269 A2 | 3/1994 |
| EP | 0 587 269 B1 | 12/1998 |
| EP | 1 255 583 B1 | 11/2002 |
| EP | 1 053 762 B1 | 8/2005 |
| EP | 2 125 100 A1 | 12/2009 |
| EP | 2 273 931 A1 | 1/2011 |
| WO | WO-2001/58520 A1 | 8/2001 |
| WO | WO-2004/066820 A2 | 8/2004 |
| WO | WO-2006/091611 A1 | 8/2006 |
| WO | WO-2006/133445 A2 | 12/2006 |
| WO | WO-2006/133445 A3 | 12/2006 |
| WO | WO-2006/135791 A2 | 12/2006 |
| WO | WO-2007/051146 A1 | 5/2007 |
| WO | WO-2007/138598 A2 | 12/2007 |
| WO | WO-2008/048471 A2 | 4/2008 |
| WO | WO-2008/070807 A2 | 6/2008 |
| WO | WO-2008/094952 A2 | 8/2008 |
| WO | WO-2008/112178 A1 | 9/2008 |
| WO | WO-2009/020764 A1 | 2/2009 |
| WO | WO-2009/134475 A1 | 11/2009 |
| WO | WO-2010/062600 A2 | 6/2010 |
| WO | WO-2010/062622 A2 | 6/2010 |
| WO | WO-2011/079866 A1 | 7/2011 |
| WO | WO-2011/112773 A2 | 9/2011 |
| WO | WO-2012/057916 A1 | 5/2012 |
| WO | WO-2012/091747 A1 | 7/2012 |
| WO | WO-2013/016268 A1 | 1/2013 |
| WO | WO-2013/019853 A1 | 2/2013 |
| WO | WO-2013/036630 A1 | 3/2013 |
| WO | WO-2013/096260 A1 | 6/2013 |
| WO | WO-2013/138786 A1 | 9/2013 |
| WO | WO-2013/155117 A1 | 10/2013 |
| WO | WO-2014/099423 A1 | 6/2014 |
| WO | WO-2015/059570 A1 | 4/2015 |
| WO | WO-2015/187426 A1 | 12/2015 |
| WO | WO-2018/007914 A1 | 1/2018 |

OTHER PUBLICATIONS

MicroProbes for Life Science, Nerve Cuff electrodes, 2018, available at https://microprobes.com/products/peripheral-electrodes/nerve-cuff, accessed Mar. 5, 2018.

Unit III—The Spine, "Motions of the Spine," available at https://courses.vcu.edu/DANC291-003/unit_3.htm, accessed Mar. 5, 2018.

Wikipedia, "Anterior superior iliac spine," Updated Feb. 12, 2018, available at https://en.wikipedia.org/wiki/Anterior_superior_iliac_spine.

Wikipedia, "Blunt Dissection," Updated Feb. 14, 2018, available at https://en.wikipedia.org/wiki/Blunt_dissection.

(56) References Cited

OTHER PUBLICATIONS

Wikipedia, "Cavernous nerves," Updated Feb. 26, 2018, available at https://en.wikipedia.org/wiki/Cavernous_nerves.
Wikipedia, "Dorsal ramus of spinal nerve," Updated Feb. 12, 2018, available at https://en.wikipedia.org/wiki/Dorsal_ramus_of_spinal_nerve.
Wikipedia, "Ventral ramus of spinal nerve," Updated Feb 12, 2018, available at https://en.wikipedia.org/wiki/Ventral_ramus_of_spinal_nerve.
International Search Report & Written Opinion dated Sep. 28, 2017 in Int'l PCT Patent Appl. Serial No. PCT/IB2017/053945.
International Search Report & Written Opinion dated Oct. 20, 2017 in Int'l PCT Patent Appl. Serial No. PCT/IB2017/053946.
Airaksinen et al., "Chapter 4. European guidelines for the management of chronic nonspecific low back pain," European spine journal [I: official publication of the European Spine Society, the European Spinal Deformity Society, and the European Section of the Cervical Spine Research Society 15 Suppl 2 (2006):S192-300. http://www.ncbi.nlm.nih.gov/pubmed/16550448.
Baker et al., "Clinical Uses of Neuromuscular Electrical Stimulation," NeuroMuscular Electrical Stimulation—A Practical Guide, 4th ed. Rancho Los Amigos Research and Education Institute Inc., pp. 47-66 (2000).
Bhadra et al., "Peripheral nerve stimulation for restoration of motor function," Journal of Clinical Neurophysiology: Official Publication of the American Electroencephalographic Society, 14(5):378-33 (Sep. 1997).
Bogie et al., "Effects of regular use of neuromuscular electrical stimulation on tissue health," Journal of Rehabilitation Research and Development, 40(6):469-475 (2003) available at: http://www.ncbi.nlm.nih.gov/pubmed/15077659 (Accessed Jan. 18, 2011).
Bowman et al., "Effects of Waveform Parameters on Comfort during Transcutaneous Neuromuscular Electrical Stimulation," Annals of Biomedical Engineering, 13:59-74 (1985).
Bradford et al., "Surface Electrical Stimulation in the Treatment of Idiopathic Scoliosis: Preliminary Results in 30 Patients," Spine, 8(7):757-764 (1983).
Brazier et al., "A Comparison of the EQ-5D and SF-6D Across Seven Patient Groups," Health Economics, 13:873-884 (2004).
Coghlan et al., "Electrical muscle stimulation for deep stabilizing muscles in abdominal wall," Conference proceedings: . . . Annual International Conference of the IEEE Engineering in Medicine and Biology Society. IEEE Engineering in Medicine and Biology Society. Conference, pp. 2756-2759 (2008) available at: http://www.ncbi.nlm.nih.gov/pubmed/19163276.
Coghlan et al., "Neuromuscular electrical stimulation training results in enhanced activation of spinal stabilizing muscles during spinal loading and improvements in pain ratings," Conference proceedings: . . . Annual International Conference of the IEEE Engineering in Medicine and Biology Society. IEEE Engineering in Medicine and Biology Society. Conference, pp. 7622-7625 (2011) available at: http://www.ncbi.nlm.nih.gov/pubmed/22256103.
Crago et al., "The choice of pulse duration for chronic electrical stimulation via surface, nerve, and intramuscular electrodes," Annals of Biomedical Engineering, 2(3):252-264 (1974).
Criterion Inc., "NMES Treatment Protocols," 3 pages (accessed Jun. 7,2012) available at http://www.criterionmed.com/PDF/NMES%20Treatment%20Protocols.pdf.
Durham et al., "Surface Electrical Stimulation Versus Brace in Treatment of Idiopathic Scoliosis," Spine, 15(9):888-891 (1990).
Empi, "Low Back Syndrome/Chronic Low Back Pain," NMES Guidelines for Treatment, 2 pages (2003).
Extended European Search Report dated Mar. 5, 2015 in EP Patent Application Serial No. 14189412.1.
Extended European Search Report dated Jan. 7, 2013 in European Patent Application Serial No. 12176863.
Ferreira et al., "Comparison of general exercise, motor control exercise and spinal manipulative therapy for chronic low back pain: A randomized trial," Pain, 131(1-2):31-37 (2007) available at: http://www.ncbi.nlm.nih.gov/pubmed/17250965.

Freeman, et al., The Role of the Lumbar Multifidus in Chronic Low Back Pain: A Review, American Academy of Physical Medicine and Rehabilitation, 2:142-146 (2010).
Friedman et al., "Electrical stimulation for scoliosis," American Family Physician, 25(4):155-160 (1982) available at: http://www.ncbi.nlm.nih.gov/pubmed/6978055 (Accessed Oct. 19, 2011).
Garmirian, et al., Discriminating Neurogenic from Myopathic Disease via Measurement of Muscle Anisotrophy, Muscle Nerve, 39(1):16-24 (2009) (Abstract only).
Gazelle et al., "Tumor Ablation with radio-frequency Energy," Radiology, (2000), 217(3):633-646.
Glaser et al., "Electrical Muscle Stimulation as an Adjunct to Exercise Therapy in the Treatment of Nonacute Low Back Pain: A Randomized Trial," The Journal of Pain, 2(5):295-300 (2001).
Gondin, et al., Electromyostimulation training effects on neural drive and muscle architecture, Med. Sci. Sports. Exerc., 37(8):1291-9 (2005).
Gorman et al., "The effect of stimulus parameters on the recruitment characteristics of direct nerve stimulation," IEEE Transactions on Bio-medical Engineering, 30(7):407-414 (1983).
Haemmerich et al., "Thermal Tumor Ablation: Devices, Clinical Applications and Future Directions," Int. J. Hyperthermia, (2005) 21(8):775-760 (Abstract only).
Hagg et al., "The Clinical Importance of Changes in Outcome Scores After Treatment for Chronic Low Back Pain," Eur. Spine. J., 12:12-20 (2003).
Herbert et al., "Scoliosis Treatment in Children Using a Programmable, Totally Implantable Muscle Stimulator (ESI)," IEEE Transactions on Biomedical Engineering, 36(7):801 (Jul. 1989).
Hodges et al., "Response of the deep paraspinal muscles to cortical but not transmastoid stimulation is increased at a single lumbar level following interverebral disc lesion," Progress in Motor Control Vi—Brazil. 36:2-3 (2007).
Hodges, et al., Intervetebral Stiffness of the Spine is Increased by Evoked Contraction of Transversus Abdominis and the Diaphragm: In Vivo Porcine Studies, Spine 28(23):2594-2601 (2003) (Abstract only).
Hodges, Is There a Role for Transversus Abdominis in Lumbo-Pelvis Stability? Manual Therapy, 4(2):74-86 (1999).
Holm, et al., Sensorimotor Control of the Spine, J. Electromyogr. Kinesiol. 12(3):219-34 (2002) (Abstract only).
Hortobagyi et al., "Neural adaptations to electrical stimulation strength training," European Journal of Applied Physiology, 2439-2449 (2011) available at: http://www.ncbi.nlm.nih.gov/pubmed/21643920 (Accessed Jul. 19, 2011).
Informal Response to Written Opinion dated Jan. 17, 2012 Int'l PCT Patent Application Serial No. PCT/US2011/027834.
International Search Report & Written Opinion dated Jan. 19, 2016 in Int'l PCT Patent Application Serial No. PCT/IB2015/055926.
International Search Report & Written Opinion dated Mar. 19, 2015 in Int'l PCT Patent Application Serial No. PCT/IB2014/002920.
International Search Report & Written Opinion dated Apr. 5, 2013 in Int'l PCT Patent Application Serial No. PCT/US2012/070259.
International Search Report & Written Opinion dated Jun. 25, 2008 in Int'l PCT Patent Appl No. PCT/US08/03126.
International Search Report and Written Opinion dated Jan. 26, 2016 in Int'l PCT Patent Application Serial No. PCT/IB2015/057838.
International Search Report and Written Opinion dated Oct. 16, 2015 in Int'l PCT Patent Application Serial No. PCT/US2015/032732.
International Search Report dated Oct. 19, 2011 in Int'l PCT Patent Application Serial No. PCT/US2011/027934.
Keller, et al., Muscular Contributions to Dynamic Dorsoventral Lumber Spine Stiffness, Eur. Spine J., 16(2):245-54 (2007).
Kiesel et al., "Measurement of lumbar multifidus muscle contraction with rehabilitative ultrasound imaging," Manual Therapy, 12(2):161-166 (2007) available at: http://www.ncbi.nlm.nih.gov/pubmed/16973400.
Lauridsen et al., "Responsiveness and Minimal Clinically Important Difference for Pain and Disability Instruments in Low Back Pain Patients," BMC Musculoskeletal Disorders, 7(82):16 pages (2006).

(56) References Cited

OTHER PUBLICATIONS

Lieber, Richard, Comparison between animal and human studies of skeletal muscle adaptation to chronic stimulation, Clinical Orthopaedics and related research, No. 233, pp. 19-24 (1988).
Lieber, Richard, Skeletal muscle adaptability. II: Muscle properties following spinal-cord injury, Developmental medicine and Child Neurology 28(4):533-42 (1986).
Lieber, Richard, Skeletal muscle adaptability. III: Muscle properties following chronic electrical stimulation, Developmental medicine and Child Neurology 28(5):662-70 (1986).
Medtronic Extension Passer 3555 Accessory Kit—Technical Instructions, 2 pages (2001).
Medtronic Interstim Therapy 3093 & 3889—Implant Manual, 38 pages (2010).
Medtronic, Kinetra, Soletra, and Itrel II, 8870, Neurostimulators for Deep Brain Stimulation (DBS), Software Application Card, Programming Guide for Software A, Dec. 1, 2003, Published 2005, Retrieved from the Internet: URL: http://www.boala-parkinson.ro/Carti%20tehnice/dbs-prog8870-gd.pdf [retrieved Aug. 23, 2018].
Medtronic Model 3464 Receiver/Extension Internalization Manual, SE-4 for Spinal Cord Stimulation (SCS), 7 pages (1986).
Medtronic Tunneling Rod Accessory Kit 8590-41—Technical Manual, 9 pages (No date available).
Miyatani, et al., Validity of Estimating Limb Muscle Volume by Bioelectrical Impedance, J. Appl. Physiol., 91:386-394 (2001).
Mortimer et al., "Intramuscular electrical stimulation: tissue damage," Annals of Biomedical Engineering, 8(3):235-244 (1980).
Mortimer et al., "Peripheral Nerve and Muscle Stimulation. In: Horch KW, Dhillon G, eds," Neuroprosthetics: Theory and Practice (Series on Bioengineering & Biomedical Engineering—vol. (2), World Scientific Publishing Company, pp. 1-48 (2005).
Nachemson et al., "Effectiveness of Treatment with a Brace in Girls Who Have Adolescent Idiopathic Scoliosis," The Journal of Bone and Joint Surgery, 77-A(6):815-819 (Jun. 1995).
Oaao Bock, "ActiGait Implantable Drop Foot Stimulator," Surgeon Manual, 28 pages (2006).
O'Donnell et al., "Electrical Stimulation in the Treatment of Idiopathic Scoliosis," Clinical Orthopaedics and Related Research, No. 229:107-112 (Apr. 1988).
Paicius et al., "Peripheral Nerve Field Stimulation for the Treatment of Chronic Low Back Pain: Preliminary Results of Long-Term Follow-up: A Case Series," Neuromodulation, 10(3):279-290 (2007) available at: http://www.blackwell-synergy.com/doi/abs/I0.IIII/j.1525-1403.2007.00116.x.
Panjabi, Manohar, "A hypothesis of chronic back pain: ligament subfailure injuries lead to muscle control dysfunction," European spine journal: official publication of the European Spine Society, the European Spinal Deformity Society, and the European Section of the Cervical Spine Research Society 15, No. 5 (May 2006): 668-676. http://www.ncbi.nlm.nih.gov/pubmed/16047209.
Panjabi, Manohar, "The stabilizing system of the spine. Part 1. Function, dysfunction, adaptation, and enhancement," Journal of Spinal Disorders, 5(4)383-389 (Dec. 1992), Discussion 397. http://www.ncbi.nlm.nih.gov/pubmed/1490034.
Panjabi, Manohar, "The stabilizing system of the spine. Part II. Neutral zone and instability hypothesis," Journal of Spinal Disorders, 5(4):390-396 (Dec. 1992), Discussion 397. http://www.ncbi.nlm.nih.gov/pubmed/1490035.
Partial International Search Report dated Aug. 4, 2015 in Int'l PCT Patent Application Serial No. PCT/US2015/032732.
PCT International Search Report and Written Opinion dated Sep. 3, 2013 in Int'l PCT Application Serial No. PCT/US2013/045223.
PCT Written Opinion dated Aug. 23, 2013 in Int'l PCT Application Serial No. PCT/US2010/049148.
Peckham et al., "Functional electrical stimulation for neuromuscular applications," Annual review of Biomedical Engineering, 7:327-360 (2005) available at: http://www.ncbi.nlm.nih.gov/pubmed/16004574.

Peterson et al., "Long-term intramuscular electrical activation of the phrenic nerve: safety and reliability," IEEE Transactions on Biomedical Engineering, 41(12):1115-1126 (1994).
Poitras et al., "Evidence-informed management of chronic low back pain with transcutaneous electrical nerve stimulation, interferential current, electrical muscle stimulation, ultrasound, and thermotherapy," The Spine Journal 8:226-233 (2008).
Reed B., "The Physiology of Neuromuscular Electrical Stimulation, Pediatric Physical Therapy," 9(3):96-102 (1997) available at: http://journals.lww.com/pedpt/pages/articleviewer.aspx?year=1997&issue=00930&article=00002&type=abstract.
Rosatelli, et al., Three-dimensional study of the musculotendinous architecture of lumbar multifidus and its functional implications, Clinical Anatomy 21(6):539-44 (2008).
RS Medical, "RS-4M Muscle Stimulator," available at http://www.rsmedical.com/documents/fact_sheet_RS4m.pdf (last visited Jul. 19, 2012).
Rutkove, "Electrical Impedance Myography: Background, Current State, and Future Directions," Muscle Nerve, 40(6):936-946 (2009).
Schwartz et al., "Therapeutic Electrical Stimulation of the Hypoglossal Nerve in Obstructive Sleep Apnea," Arch Otolaryngal Head Neck Surg., 127:1216-1223 (2001).
Sheffler et al., "Neuromuscular Electrical Stimulation in Neurorehabilitation," Muscle Nerve, 35: 562-590 (2007).
Sippl, Charles J., "Computer Dictionary: Third Edition," pp. 2257 and 340.
Sluijter, "Radiofrequency Ablation in the Management of Spinal Pain," C212, (2006), IV(1):10-15.
Solomonow et al., "The Ligamento-Muscular Stabilizing System of the Spine," Spine, (1998), 23(23):2552-2562.
Spinal Fusion Guidelines, MD Guidelines, 2009. www.mdguidelines.com/spinal-fusion.
Stokes, et al., "Surface EMG Electrodes Do Not Accurately Record from Lumbar Multifidus Muscles," Clin. Biomech, (2003), 18(1):9-13 (Abstract Only).
Van Dieen, et al., "Trunk Muscle Recruitment Patterns," Spine, (2003), 28(8):834-841 (Abstract Only).
Van et al., "The use of real-time ultrasound imaging for biofeedback of lumbar multifidus muscle contraction in healthy subjects," The Journal of Orthopaedic and Sports Physical Therapy, 36(12):920-925 (2006) available at: http://www.ncbi.n1m.nih.gov/pubmed/17193869.
Van Zundert et al., "Radiofrequency treatment for chronic pain syndromes," CPD Anaesthesis, 6(1):13-17 (2004).
Verrills et al., "Peripheral Nerve Stimulation: A Treatment for Chronic Low Back Pain and Failed Back Surgery Syndrome?," Neuromodulation: Technology at the Neural Interface, (2009), 12(1):68-75.
Vrbova et al., Application of Muscle/Nerve Stimulation in Health and Disease, Springer Verlag (2008) available at: http://books.google.com/books?hl=en&lr=&id=jb8fDGxkbqEC&oi=fnd&pg=PAl&dq=Application of Muscle/Nerve Stimulation in Health and Disease&ots=CMV5rXiDQD&sig=Wg8u1YOC4PgvVDzcjdwBub5U2To (Accessed Jun. 2, 2011).
Wallwork et al., "The effect of chronic low back pain on size and contraction of the lumbar multifidus muscle," Manual Therapy, 14(5):496-500 (2009) available at: http://www.ncbi.nlm.nih.gov/pubmed/19027343.
Ward et al., "Architectural analysis and intraoperative measurements demonstrate the unique design of the multifidus for lumbar spine stability," J. Bone Joint Surg. [Am.] 91:176-185, PMC2663324 (2009).
Wikipedia, "Interference Fit," http://en.wikipedia.org/wiki/Interference_fit, accessed Dec. 4, 2014.
Wikipedia, "Time-division multiplexing," https://en.wikipedia.org/wiki/Time-division_multiplexing (accessed Nov. 12, 2015).
Wright et al., "Morphologic and histochemical characteristics of skeletal muscle after long-term intramuscular electrical stimulation," Spine, 17(7):767-770 (1992) available at: http://www.ncbi.nlm.nih.gov/pubmed/1502640 (Accessed Aug. 2, 2011).

(56) References Cited

OTHER PUBLICATIONS

Written Opinion dated Nov. 16, 2011 in Int'l PCT Patent Application Serial No. PCT/US2011/027934.

* cited by examiner

SYSTEMS AND METHODS FOR ENHANCED IMPLANTATION OF ELECTRODE LEADS BETWEEN TISSUE LAYERS

I. FIELD OF THE INVENTION

This application generally relates to systems and methods for implanting electrode leads for neuromuscular electrical stimulation, including stimulation of tissue associated with control of the lumbar spine for treatment of back pain.

II. BACKGROUND OF THE INVENTION

The human back is a complicated structure including bones, muscles, ligaments, tendons, nerves and other structures. The spinal column has interleaved vertebral bodies and intervertebral discs, and permits motion in several planes including flexion-extension, lateral bending, axial rotation, longitudinal axial distraction-compression, anterior-posterior sagittal translation, and left-right horizontal translation. The spine provides connection points for a complex collection of muscles that are subject to both voluntary and involuntary control.

Back pain in the lower or lumbar region of the back is common. In many cases, the cause of back pain is unknown. It is believed that some cases of back pain are caused by abnormal mechanics of the spinal column. Degenerative changes, injury of the ligaments, acute trauma, or repetitive microtrauma may lead to back pain via inflammation, biochemical and nutritional changes, immunological factors, changes in the structure or material of the endplates or discs, and pathology of neural structures.

The spinal stabilization system may be conceptualized to include three subsystems: 1) the spinal column, which provides intrinsic mechanical stability; 2) the spinal muscles, which surround the spinal column and provide dynamic stability; and 3) the neuromotor control unit, which evaluates and determines requirements for stability via a coordinated muscle response. In patients with a functional stabilization system, these three subsystems work together to provide mechanical stability. It is applicant's realization that low back pain results from dysfunction of these subsystems.

The spinal column consists of vertebrae and ligaments, e.g. spinal ligaments, disc annulus, and facet capsules. There has been an abundance of in-vitro work in explanted cadaver spines and models evaluating the relative contribution of various spinal column structures to stability, and how compromise of a specific column structure will lead to changes in the range of motion of spinal motion segments.

The spinal column also has a transducer function, to generate signals describing spinal posture, motions, and loads via mechanoreceptors present in the ligaments, facet capsules, disc annulus, and other connective tissues. These mechanoreceptors provide information to the neuromuscular control unit, which generates muscle response patterns to activate and coordinate the spinal muscles to provide muscle mechanical stability. Ligament injury, fatigue, and viscoelastic creep may corrupt signal transduction. If spinal column structure is compromised, due to injury, degeneration, or viscoelastic creep, then muscular stability must be increased to compensate and maintain stability.

Muscles provide mechanical stability to the spinal column. This is apparent by viewing cross section images of the spine, as the total area of the cross sections of the muscles surrounding the spinal column is larger than the spinal column itself. Additionally, the muscles have much larger lever arms than those of the intervertebral disc and ligaments.

Under normal circumstances, the mechanoreceptors exchange signals with the neuromuscular control unit for interpretation and action. The neuromuscular control unit produces a muscle response pattern based upon several factors, including the need for spinal stability, postural control, balance, and stress reduction on various spinal components.

It is believed that in some patients with back pain, the spinal stabilization system is dysfunctional. With soft tissue injury, mechanoreceptors may produce corrupted signals about vertebral position, motion, or loads, leading to an inappropriate muscle response. In addition, muscles themselves may be injured, fatigued, atrophied, or lose their strength, thus aggravating dysfunction of the spinal stabilization system. Conversely, muscles can disrupt the spinal stabilization system by going into spasm, contracting when they should remain inactive, or contracting out of sequence with other muscles. As muscles participate in the feedback loop via mechanoreceptors in the form of muscle spindles and golgi tendon organs, muscle dysfunction may further compromise normal muscle activation patterns via the feedback loops.

Trunk muscles may be categorized into local and global muscles. The local muscle system includes deep muscles, and portions of some muscles that have their origin or insertion on the vertebrae. These local muscles control the stiffness and intervertebral relationship of the spinal segments. They provide an efficient mechanism to fine-tune the control of intervertebral motion. The lumbar multifidus, with its vertebra-to-vertebra attachments is an example of a muscle of the local system. Another example is the transverse abdominus, with its direct attachments to the lumbar vertebrae through the thoracolumbar fascia. The thoracolumbar fascia is a deep investing membrane which covers the deep muscles of the back of the trunk. The thoracolumbar fascia includes superficial fascia and deep fascia. The superficial fascia is traditionally regarded as a layer of areolar connective or adipose tissue immediately beneath the skin, whereas deep fascia is a tougher, dense connective tissue continuous with it. Deep fascia is commonly arranged as sheets and typically forms a stocking around the muscles and tendons beneath it. Superficial fascia fibers run in the transverse direction, whereas deep fascia fibers run in a cranial-caudal direction.

The multifidus is the largest and most medial of the lumbar back muscles. It has a repeating series of fascicles which stem from the laminae and spinous processes of the vertebrae, and exhibit a constant pattern of attachments caudally. These fascicles are arranged in five overlapping groups such that each of the five lumbar vertebrae gives rise to one of these groups. At each segmental level, a fascicle arises from the base and caudolateral edge of the spinous process, and several fascicles arise, by way of a common tendon, from the caudal tip of the spinous process. Although confluent with one another at their origin, the fascicles in each group diverge caudally to assume separate attachments to the mamillary processes, the iliac crest, and the sacrum. Some of the deep fibers of the fascicles that attach to the mamillary processes attach to the capsules of the facet joints next to the mamillary processes. The fascicles arriving from the spinous process of a given vertebra are innervated by the medial branch of the dorsal ramus that issues from below that vertebra. The dorsal ramus is part of spinal nerve roots formed by the union of dorsal root fibers distal to the dorsal root ganglion and ventral root fibers. The dorsal root ganglion is a collection of sensory neurons that relay sensory information from the body to the central nervous system.

The global muscle system encompasses the large, superficial muscles of the trunk that cross multiple motion segments, and do not have direct attachment to the vertebrae. These muscles are the torque generators for spinal motion, and control spinal orientation, balance the external loads applied to the trunk, and transfer load from the thorax to the pelvis. Global muscles include the oblique internus abdominus, the obliquus externus abdmonimus, the rectus abdominus, the lateral fibers of the quadratus lumborum, and portions of the erector spinae.

Normally, load transmission is painless. Over time, dysfunction of the spinal stabilization system is believed to lead to instability, resulting in overloading of structures when the spine moves beyond its neutral zone. The neutral zone is a range of intervertebral motion, measured from a neutral position, within which the spinal motion is produced with a minimal internal resistance. High loads can lead to inflammation, disc degeneration, facet joint degeneration, and muscle fatigue. Since the endplates and annulus have a rich nerve supply, it is believed that abnormally high loads may be a cause of pain. Load transmission to the facets also may change with degenerative disc disease, leading to facet arthritis and facet pain.

For patients believed to have back pain due to instability, clinicians offer treatments intended to reduce intervertebral motion. Common methods of attempting to improve muscle strength and control include core abdominal exercises, use of a stability ball, and Pilates. Spinal fusion is the standard surgical treatment for chronic back pain. Following fusion, motion is reduced across the vertebral motion segment. Dynamic stabilization implants are intended to reduce abnormal motion and load transmission of a spinal motion segment, without fusion. Categories of dynamic stabilizers include interspinous process devices, interspinous ligament devices, and pedicle screw-based structures. Total disc replacement and artificial nucleus prostheses also aim to improve spine stability and load transmission while preserving motion.

There are a number of problems associated with current implants that aim to restore spine stabilization. First, it is difficult to achieve uniform load sharing during the entire range of motion if the location of the optimum instant axis of rotation is not close to that of the motion segment during the entire range of motion. Second, cyclic loading of dynamic stabilization implants may cause fatigue failure of the implant, or the implant-bone junction, e.g. screw loosening. Third, implantation of these systems requires surgery, which may cause new pain from adhesions, or neuroma formation. Moreover, surgery typically involves cutting or stripping ligaments, capsules, muscles, and nerve loops, which may interfere with the spinal stabilization system.

Functional electrical stimulation (FES) is the application of electrical stimulation to cause muscle contraction to re-animate limbs following damage to the nervous system such as with stroke or spine injury. FES has been the subject of much prior art and scientific publications. In FES, the goal generally is to bypass the damaged nervous system and provide electrical stimulation to nerves or muscles directly which simulates the action of the nervous system. One lofty goal of FES is to enable paralyzed people to walk again, and that requires the coordinated action of several muscles activating several joints. The challenges of FES relate to graduation of force generated by the stimulated muscles, and the control system for each muscle as well as the system as a whole to produce the desired action such as standing and walking.

With normal physiology, sensors in the muscle, ligaments, tendons and other anatomical structures provide information such as the force a muscle is exerting or the position of a joint, and that information may be used in the normal physiological control system for limb position and muscle force. This sense is referred to as proprioception. In patients with spinal cord injury, the sensory nervous system is usually damaged as well as the motor system, and thus the afflicted person loses proprioception of what the muscle and limbs are doing. FES systems often seek to reproduce or simulate the damaged proprioceptive system with other sensors attached to a joint or muscle.

For example, in U.S. Pat. No. 6,839,594 to Cohen, a plurality of electrodes are used to activate selected groups of axons in a motor nerve supplying a skeletal muscle in a spinal cord patient (thereby achieving graduated control of muscle force) and one or more sensors such as an accelerometer are used to sense the position of limbs along with electrodes attached to muscles to generate an electromyogram (EMG) signal indicative of muscle activity. In another example, U.S. Pat. No. 6,119,516 to Hock, describes a biofeedback system, optionally including a piezoelectric element, which measures the motions of joints in the body. Similarly a piezoelectric crystal may be used as a muscle activity sensor as described by U.S. Pat. No. 5,069,680 to Grandjean.

FES has also been used to treat spasticity, characterized by continuous increased muscle tone, involuntary muscle contractions, and altered spinal reflexes which leads to muscle tightness, awkward movements, and is often accompanied by muscle weakness. Spasticity results from many causes including cerebral palsy, spinal cord injury, trauma, and neurodegenerative diseases. U.S. Pat. No. 7,324,853 to Ayal describes apparatus and method for electrically stimulating nerves that supply muscles to modify the muscle contractions that lead to spasticity. The apparatus includes a control system configured to analyze electrical activity of one or more muscles, limb motion and position, and mechanical strain in an anatomical structure.

Neuromuscular Electrical Stimulation (NMES) is a subset of the general field of electrical stimulation for muscle contraction, as it is generally applied to nerves and muscles which are anatomically intact, but malfunctioning in a different way. NMES may be delivered via an external system or, in some applications, via an implanted system.

NMES via externally applied skin electrodes has been used to rehabilitate skeletal muscles after injury or surgery in the associated joint. This approach is commonly used to aid in the rehabilitation of the quadriceps muscle of the leg after knee surgery. Electrical stimulation is known to not only improve the strength and endurance of the muscle, but also to restore malfunctioning motor control to a muscle. See, e.g., Gondin et al., "Electromyostimulation Training Effects on Neural Drive and Muscle Architecture", Medicine & Science in Sports & Exercise 37, No. 8, pp. 1291-99 (August 2005).

An implanted NMES system has been used to treat incontinence by stimulating nerves that supply the urinary or anal sphincter muscles. For example, U.S. Pat. No. 5,199,430 to Fang describes implantable electronic apparatus for assisting the urinary sphincter to relax.

The goals and challenges of rehabilitation of anatomically intact (i.e., non-pathological) neuromuscular systems are fundamentally different from the goals and challenges of FES for treating spinal injury patients or people suffering from spasticity. In muscle rehabilitation, the primary goal is to restore normal functioning of the anatomically intact neuromuscular system, whereas in spinal injury and spasticity, the primary goal is to simulate normal activity of a pathologically damaged neuromuscular system.

U.S. Pat. Nos. 8,428,728 and 8,606,358 to Sachs, both assigned to the assignee of the present disclosure, and both incorporated herein in their entireties by reference, describe implanted electrical stimulation devices that are designed to restore neural drive and rehabilitate the multifidus muscle to improve stability of the spine. Rather than masking pain signals while the patient's spinal stability potentially undergoes further deterioration, the stimulator systems described in those applications are designed to reactivate the motor control system and/or strengthen the muscles that stabilize the spinal column, which in turn is expected to reduce persistent or recurrent pain.

While the stimulator systems described in the Sachs patents seek to rehabilitate the multifidus and restore neural drive, use of those systems necessitates the implantation of one or more electrode leads in the vicinity of a predetermined anatomical site, such as the medial branch of the dorsal ramus of the spinal nerve to elicit contraction of the lumbar multifidus muscle. For lead implantation using the Seldinger technique, it has been proposed to insert a needle in the patient's back, insert a guidewire through a lumen in the needle, remove the needle, insert a sheath over the guidewire, remove the guidewire, insert the electrode lead through a lumen of the sheath, and remove the sheath. Such a process can result in complications depending on the insertion site due to anatomical structures surrounding the target implantation site, impeding the insertion path. For example, as discussed above, the deep back muscles are covered by the thoracolumbar fascia which comprises superficial fascia running in the transverse direction and deep fascia running in a cranial-caudal direction. There is a risk that electrode lead conductors may experience a tight bend near the location where the lead enters the thoracolumbar fascia when the lead is inserted within the body near the lateral edge of the spine. Such a tight bend may lead to dislodgement of the electrode lead and/or fracture, thereby preventing proper therapy delivery. The difference in directions of the superficial and deep fascia near the insertion site at the lateral edge of the spine may increase the risk of a high stress location on the lead.

It would therefore be desirable to provide systems and methods for implanting an electrode lead to rehabilitate muscle associated with control of the lumbar spine to treat back pain with reduced risk of a high stress location on the lead and dislodgement of the electrode lead by surrounding anatomical structures.

III. SUMMARY OF THE INVENTION

The present disclosure describes systems and methods for enhanced implantation of an electrode lead between tissue layers to reduce the risks of a high stress location on the lead or dislodgement. The lead may be configured to emit electrical energy from one or more electrodes disposed on the lead to stimulate target tissue to restore muscle function to the lumbar spine and treat, for example, low back pain. The systems and methods are expected to provide efficient implantation of the lead in a midline-to-lateral manner such that the implanted lead may be secured within the patient and used to restore muscle function of local segmental muscles associated with the lumbar spine stabilization system without disruption of the electrode lead post-implantation due to surrounding anatomical structures.

In accordance with one aspect of the present disclosure, a method for restoring muscle function to a lumbar spine is provided. The method includes selecting a guide needle having a longitudinal axis and a distal tip, a delivery needle having a distal tip, a lumen and a longitudinal axis, and a lead having a distal region including one or more electrodes.

First, a target vertebrae of the lumbar spine is located. For example, the target vertebrae may be the L3 vertebrae. Next, the distal tip of the guide needle is inserted percutaneously at a first insertion site a lateral distance from a midline of the target vertebrae to a depth. The first insertion site may be located at a cranial edge of a transverse process of the target vertebrae, proximately lateral to a base of a superior articular process of the target vertebrae. The method may also include measuring the depth attained by the distal tip of the guide needle.

A second insertion site along the midline of the target vertebrae is then located based on the depth. Accordingly, the second insertion site may be located along the midline of the target vertebrae at a distance from the first insertion site approximately equal to the depth measured. As such, the second insertion site may be located above an L4 spinous process.

Next, the method may include inserting the distal tip of a delivery needle percutaneously at the second insertion site such that the longitudinal axis of the delivery needle is angled relative to the longitudinal axis of the guide needle, e.g., about 45 degrees, so as to traverse naturally occurring fascicle planes. The method may also include visualizing the distal tip of the delivery needle within an outline of a neural foramen of the target vertebrae to confirm proper placement. The distal tip of the delivery needle may be advanced approximately 3-5 mm beyond the distal tip of the guide needle, thereby penetrating tissue for lead anchoring, e.g., muscle such as the intertransversarii.

Next, a guidewire is advanced through the lumen of the delivery needle. The guide needle may be removed after the distal tip of the delivery needle is inserted percutaneously at the second insertion site.

Next, the delivery needle is removed and an introducer assembly is advanced over the guidewire. The introducer assembly may include a dilator having a lumen extending therethrough configured to receive the guidewire, and an introducer sheath having a lumen extending therethrough configured to receive the dilator. The distal tip of the introducer assembly may be visualized within an outline of a neural foramen of the target vertebrae to confirm placement of the introducer assembly within a plane of the lead anchor site, e.g., a plane of muscle such as the intertransversarii. The guidewire is then removed, and if a dilator is used, the dilator may be removed after the guidewire is removed.

The lead is then advanced through the introducer assembly so that the one or more electrodes are disposed in or adjacent to the tissue associated with control of the lumbar spine, e.g., nervous tissue such as the dorsal ramus nerve or fascicles thereof. The lead may include one or more fixation elements disposed in proximity to at least one of the one or more electrodes. The one or more fixation elements may be configured to transition from a delivery state, wherein the one or more fixation elements are positioned adjacent to at least one of the one or more electrodes, to a deployed state, wherein the one or more fixation elements are spaced apart from at least one of the one or more electrodes and positioned to anchor the lead to the anchor site e.g., muscle such as the intertransversarii.

Next, the introducer assembly is retracted, which may cause the one or more fixation elements to transition from the delivery state to the deployed state. For example, the fixation elements may be formed of a flexible material, e.g., a polymer, and may be biased to self-expand to the deployed state when exposed from the introducer assembly.

Finally, an implantable pulse generator that is configured to be coupled to the lead may be implanted within the patient body. The proximal end of the lead may be subcutaneously tunneled to the IPG using a tunneler system.

In accordance with another aspect of the present disclosure, a kit for implanting a device for restoring muscle function to a lumbar spine is provided. The kit may include a guide needle having a distal tip and a longitudinal axis; a delivery needle having a distal tip and a lumen extending therethrough; a guidewire configured to be inserted through the lumen of the delivery needle; an introducer assembly having a distal tip and a lumen extending therethrough configured to receive the guidewire; and a lead having one or more electrodes disposed at a distal region of the lead, as described above.

The kit may further include an implantable pulse generator configured to be coupled to the one or more electrodes via the lead.

IV. BRIEF DESCRIPTION OF THE DRAWINGS

V. DETAILED DESCRIPTION OF THE INVENTION

The systems and methods of the present disclosure may provide efficient implantation of an electrode lead in a midline-to-lateral manner such that the implanted lead may be secured within the patient and used to restore muscle function of local segmental muscles associated with the lumbar spine stabilization system without disruption of the electrode lead post-implantation due to surrounding anatomical structures. In accordance with the principles of the present disclosure, the systems and methods may be optimized for use in restoring muscle function to the lumbar spine to treat, for example, low back pain.

Figure 1A:
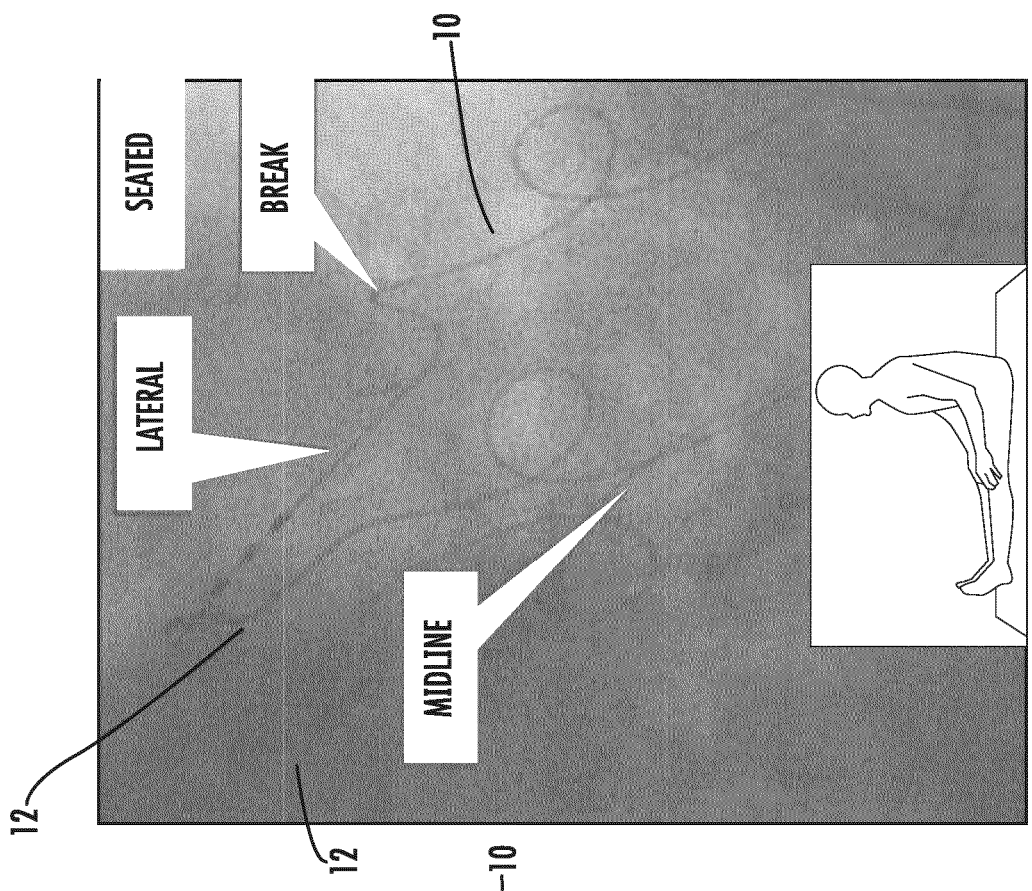
FIGS. 1A and 1B illustrate electrode leads implanted via a midline insertion and a lateral insertion within a patient body, where the electrode leads are shown when the patient body is in a supine position in FIG. 1A and in a seated position in FIG. 1B.
Figure 1B:
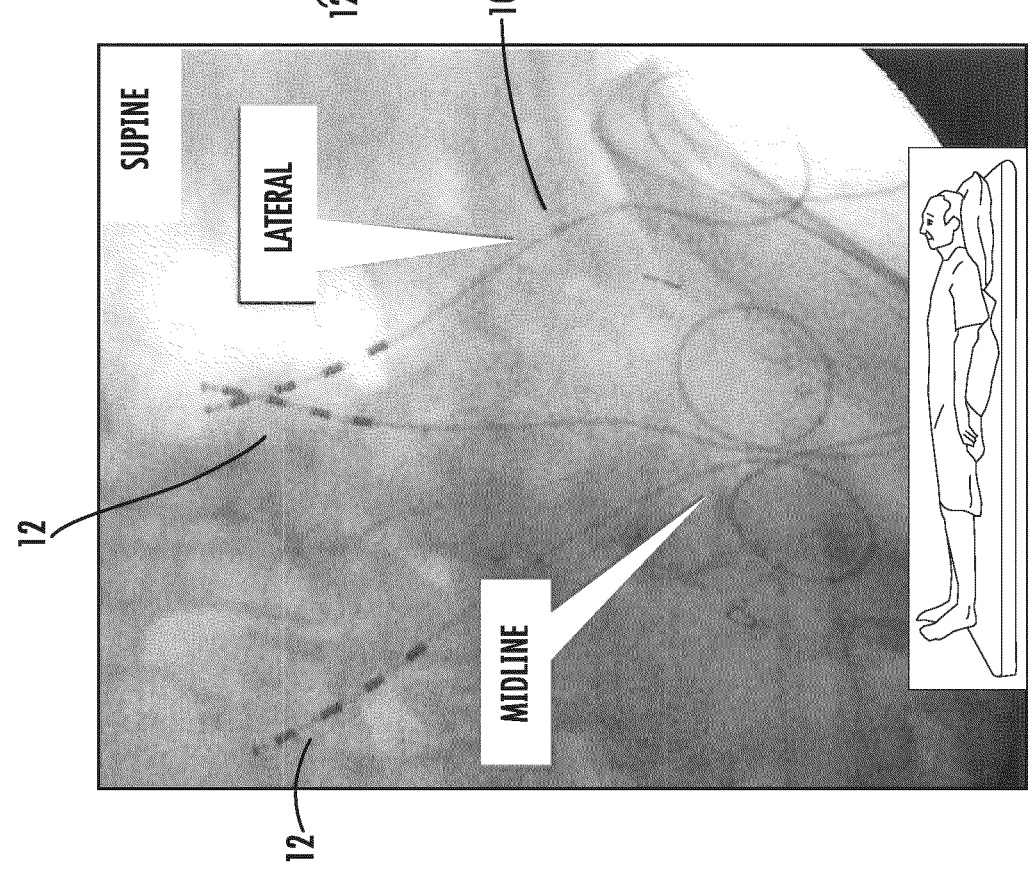

Referring to FIGS. 1A and 1B, a comparison of traditional implantation methods and the exemplary method in accordance with the principles of the present disclosure is provided. FIGS. 1A and 1B illustrate x-ray images of the lumbar region of a cadaver with electrode lead 10 and electrode leads 12 implanted therein. Electrode lead 10 was implanted via traditional methods of lead implantation utilizing a lateral incision, whereas electrode leads 12 were implanted via the exemplary method in accordance with the principles of the present disclosure. FIG. 1A depicts electrode lead 10 and electrode leads 12 implanted in the cadaver while the cadaver is in a supine (laying down) position, while FIG. 1B depicts electrode lead 10 and electrode leads 12 implanted in the cadaver while the cadaver is in a seated position to reflect the various positions a potential living patient would experience on a day-to-day basis. Both electrode lead 10 and electrode leads 12 are depicted with strain relief portions to reduce further stress on the respective leads, as described in more detail below.

As shown in FIG. 1B, electrode lead 10 experiences a tight bend along the lead body distal to the strain relief portion of the lead, whereas electrode leads 12 lack any such tight bend. It is believed that the tight bend observed in electrode lead 10 results from the trajectory from the incision site to the target implantation location. Specifically, as described above, the superficial fascia fibers run in the transverse direction, whereas deep fascia fibers run in a cranial-caudal direction, which provides a crisscross environment of the thoracolumbar fascia in the proximity of the traditional implantation trajectory. This crisscross environment applies forces on the lead body resulting in the observed tight bend. In contrast, electrode leads 12 are implanted with a trajectory from an insertion site located along the midline of the vertebrae toward the target implantation location lateral to the midline. Thus, the exemplary method of the present disclosure provides an implantation trajectory that avoids the problematic crisscross environment provided by the thoracolumbar fascia, and reduces the risk of a high stress location on the lead observed in traditional implantation methods.

Figure 2:
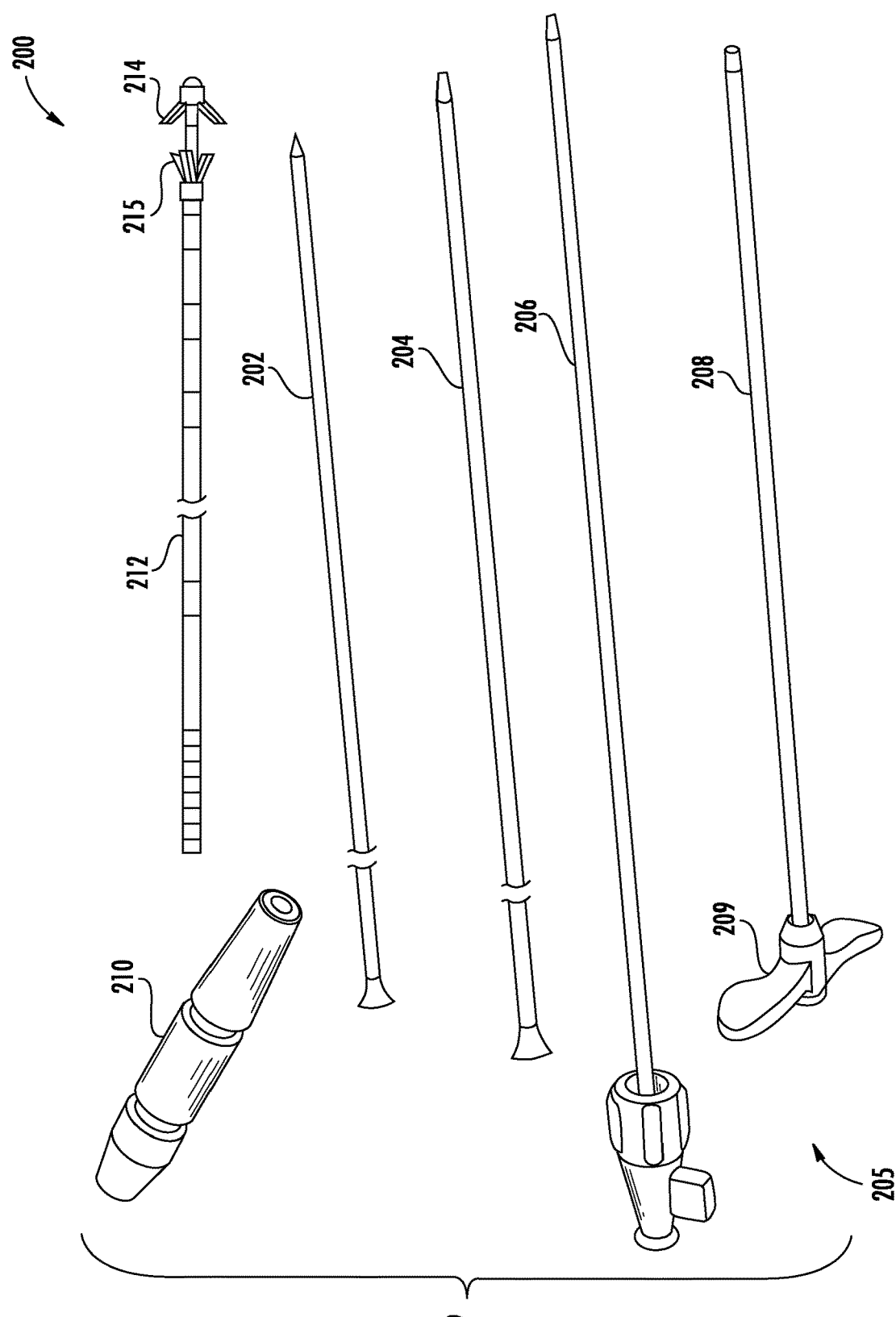
FIG. 2 shows an exemplary kit for delivering an electrode lead in accordance with the principles of the present disclosure.

Referring now to FIG. 2, an exemplary kit for implanting an electrode lead is described. In FIG. 2, components of the kit are not depicted to scale on either a relative or absolute basis.

Kit 200 may include guide needle 202, delivery needle 204, a guidewire, introducer assembly 205, electrode lead 212, suture sleeve 210 and an implantable pulse generator (IPG). Guide needle 202 includes a distal tip and a longitudinal axis. The distal tip of guide needle 202 may be beveled to ease introduction through tissue. Delivery needle 204 includes a distal tip and a lumen extending therethrough shaped and sized to receive a guidewire. The distal tip of delivery needle 204 may be beveled to ease introduction through tissue. The guidewire is configured to be inserted through the lumen of delivery needle 204.

Introducer assembly 205 includes a distal tip and a lumen extending therethrough configured to receive the guidewire. The distal tip of introducer assembly 205 may be beveled to ease introduction through tissue. Introducer assembly 205 may include introducer sheath 208, which has a lumen extending therethrough configured to receive electrode lead 212. Introducer sheath 208 may include handle 209 sized and shaped to permit a clinician to comfortably hold introducer sheath 208. Introducer assembly 205 also may include dilator 206, which has a lumen extending therethrough configured to receive the guidewire. The lumen of introducer sheath 208 may be shaped and sized to permit dilator 206 to slide therethrough, and the lumen of dilator 206 also serves as the lumen of introducer assembly 205. Further in this embodiment, introducer sheath 208 has a coupling portion configured to be coupled to a portion of dilator 206. In addition, when dilator 206 is removed from within the lumen of introducer sheath 208, the lumen of introducer sheath 208 may receive electrode lead 212.

Electrode lead 212 may include a distal region having one or more electrodes disposed thereon that are configured to be implanted in or adjacent to tissue, such as nervous tissue, muscle, ligament, and/or joint capsule. Electrode lead 212 is a suitable length for positioning the electrodes in or adjacent to target tissue while the IPG is implanted in a suitable location, e.g., the lower back. For example, electrode lead 212 may be between about 30 and 80 cm in length, and preferably about 45 or about 65 cm in length. Electrode lead 212 is also of a suitable diameter for placement, for example, between about 1 and 2 mm in diameter and preferably about 1.3 mm.

The one or more electrodes may be configured to stimulate the tissue at a stimulation frequency and at a level and duration sufficient to cause muscle to contract and may be ring electrodes, partial electrodes, segmented electrodes, nerve cuff electrodes placed around the nerve innervating the target muscle, or the like. For example, the one or more electrodes may be implanted in or adjacent to nervous tissue associated with a target muscle(s). The one or more electrodes may be implanted in or adjacent to the dorsal ramus nerve, or fascicles thereof, innervating the multifidus muscle. In such embodiments, the one or more electrodes are configured to emit electrical energy to stimulate the dorsal ramus nerve, or fascicles thereof, to cause the multifidus to contract to thereby rehabilitate the multifidus and increase stability of the lumbar spine to reduce back pain. The one or more electrodes are a suitable length(s) and spaced apart a suitable distance along the distal region of electrode lead 212. For example, the one or more electrodes may be about 2-5 mm in length, and preferably about 3 mm, and may be spaced apart about 2-6 mm, and preferably about 4 mm.

Electrode lead 212 may further include fixation elements 214 and 215 disposed in proximity to at least one of the one or more electrodes. As will also be understood by one of skill in the art, fixation elements 214 and 215 may be positioned along the electrode lead to secure any one of the other electrodes disposed thereon at a target implantation location. Electrode lead 212 also may be structurally similar to any of the electrode leads described in U.S. Ser. No. 15/202,435, U.S. Pat. No. 9,072,897 to Sachs, U.S. Pat. No. 9,079,019 to Crosby, U.S. Patent Application Pub. No. 2013/0338730 to Shiroff, U.S. Patent Application Pub. No. 2014/0350653 to Shiroff, and/or U.S. Pat. No. 9,186,501 to Rawat, each assigned to the assignee of the present disclosure, the entire contents of each of which are incorporated herein by reference. As such, fixation elements 214 and 215 may be positioned adjacent to at least one of the one or more electrodes of electrode lead 212 in a delivery state, or may be spaced apart from the one or more electrodes of electrode lead 212 in a deployed state. In the deployed state, fixation elements 214 and 215 may be positioned to anchor electrode lead 212 to an anchor site, e.g., muscle such as the intertransversarii. Fixation elements 214 and 215 may be formed of a flexible material, e.g., a polymer, and may be biased to self-expand to the deployed state when exposed from the introducer assembly. Fixation elements 214 and 215 may include any number of projections, generally between 1 and 8 each and preferably 3 or 4 each. The length of and spacing between fixation elements 214 and 215 are defined by the structure around which they are to be placed. In one embodiment, the length of the projections of fixation elements 214 and 215 is between about 1.5-4 mm and preferably about 2.5 mm and the spacing between fixation elements 214 and 215 is between about 2 mm and 10 mm and preferably about 6 mm.

In one embodiment, fixation elements 214 may be configured to be radially offset relative to fixation elements 215 by prefabricating at least one of fixation elements 214 and fixation elements 215 relative to electrode lead 212 such that the projections of fixation elements 214 are radially offset relative to the projections of fixation elements 215 as illustrated and described in further detail in U.S. Ser. No. 15/202,435. For example, the projections of fixation elements 214 may be radially offset relative to the projections of fixation elements 215 by a predetermined angle, e.g., approximately 60 degrees. However, as appreciated by one of ordinary skill in the art, the projections of fixation elements 214 may be radially offset relative to the projections of fixation elements 215 by other angles to achieve the benefits in accordance with the present disclosure.

While FIG. 2 illustrates electrode lead 212 having fixation elements 214 and 215, it should be understood that other fixation elements may be used to anchor electrode lead 212 at a suitable location including the fixation elements described in U.S. Pat. No. 9,079,019 to Crosby and U.S. Patent Application Pub. No. 2013/0338730 to Shiroff, both assigned to the assignee of the present disclosure, the entire contents of each of which are incorporated herein by reference.

In one embodiment, kit 200 may further include a stylet and electrode lead 212 may further include a stylet lumen extending therethrough. The stylet lumen is shaped and sized to permit a stylet to be inserted therein, for example, during delivery of electrode lead 212 to provide additional stiffness to electrode 212.

Suture sleeve 210 may optionally be provided to secure at least a portion of electrode lead 212 percutaneously under the skin of the patient body. Suture sleeve 210 illustratively includes a first end section, a middle section separated from first end section by a first groove, a second end section separated from the middle section by a second groove, and a sleeve lumen extending therethrough. The first and second end sections may have truncated conical portions as shown. The first and second grooves are sized and shaped to accept sutures such that suture sleeve 210 may be secured to tissue, e.g., superficial fascia, using the sutures. The lumen of suture sleeve 210 is sized such that electrode lead 212 may be inserted therethrough.

The IPG is configured to be coupled to a proximal end of electrode lead 212, e.g., using a tunneler system such as that described in U.S. Ser. No. 15/202,435, and to provide electrical stimulation via the one or more electrodes of electrode lead 212. The internal functional components of the IPG may be structurally similar to the IPG described in U.S. Pat. No. 9,072,897 to Sachs.

Figure 3:
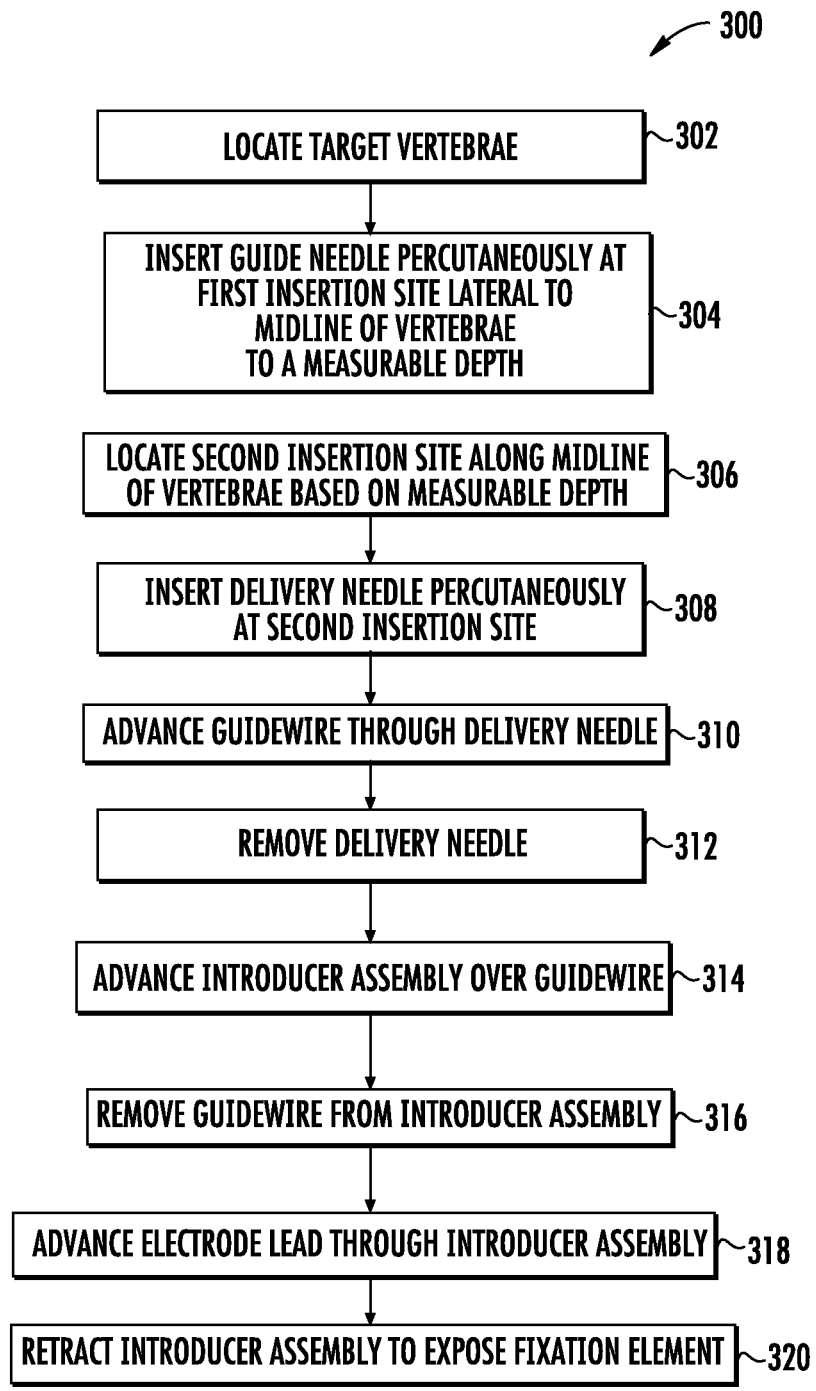
FIG. 3 illustrates a flow chart of an exemplary method for implanting an electrode lead at a target location in accordance with the principles of the present disclosure.

Referring now to FIGS. 3 and 4A-4J, an exemplary method using the kit described above to implant an electrode lead in accordance with the principles of the present disclosure is described. Specifically, FIG. 3 illustrates exemplary method 300 for implanting electrode lead 212 at a target implantation location, e.g., in or adjacent to tissue associated with control of the lumbar spine. For example, the electrode lead may be implanted such that the one or more electrodes are positioned to stimulate the dorsal ramus nerve, or fascicles thereof, that innervate the multifidus muscle. FIGS. 4B and 4D-4J depict a lateral projection of a segment of a typical human lumbar spine shown having a vertebral body V, transverse process TP, intertransversarii ITV, a dorsal ramus DR nerve, and a dorsal root ganglion DRG.

Referring back to FIG. 3 and FIG. 4A, step 302 is described. At 302, the clinician locates the target vertebrae. The target vertebrae is the vertebrae of the patient body associated with the target implantation site. In one embodiment, the target vertebrae may be the L3 vertebrae. The clinician may locate the target vertebrae manually by using his or her fingers to count vertebra-by-vertebra from an identifiable starting location, e.g., the sacrum or the L5 vertebrae. Alternatively, the clinician may use any other method known in the art to identify a target vertebrae, e.g., a visualization technique such as x-ray.

Figure 4A:
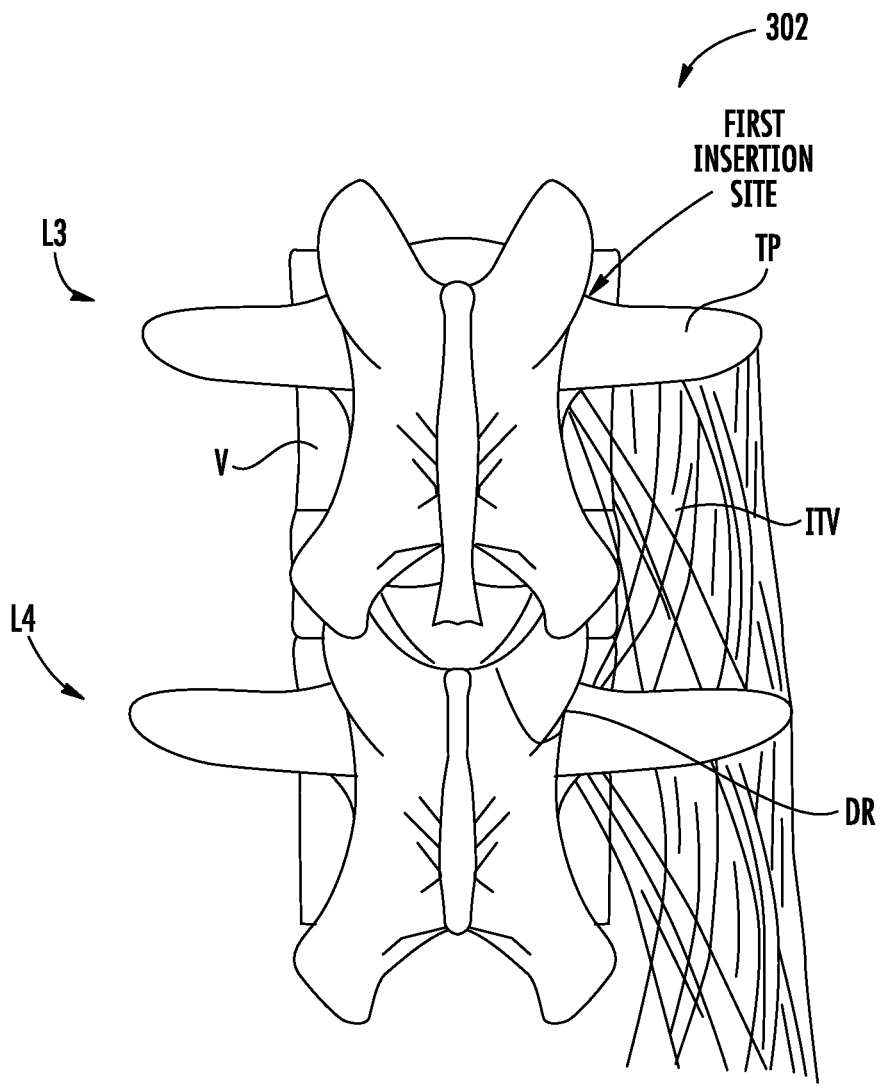
FIGS. 4A through 4J show an exemplary method for implanting an electrode lead and IPG using the kit of FIG. 2.
Figure 4B:
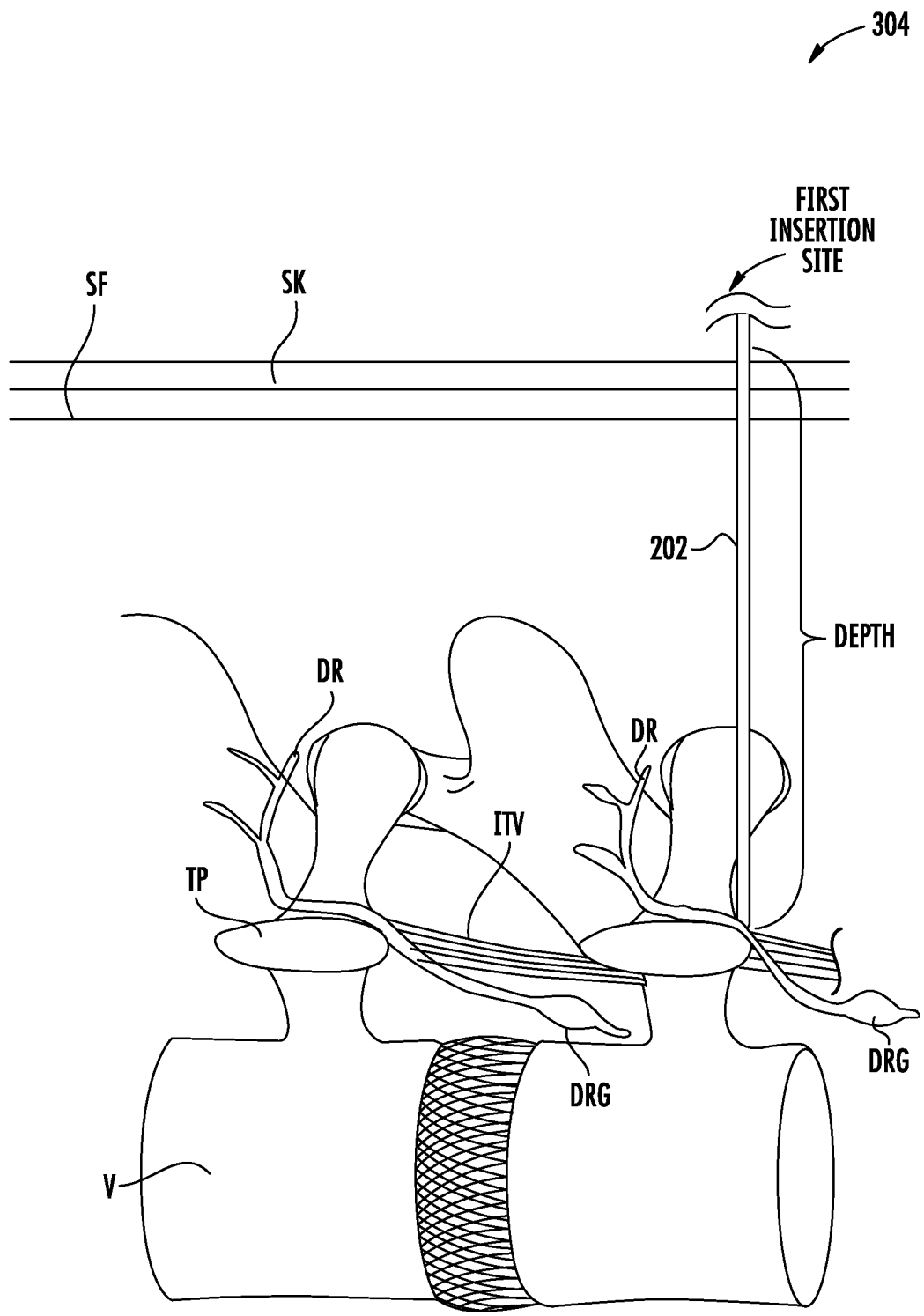

Referring back to FIG. 3 and now to FIG. 4B, step 304 is described. At 304, the clinician inserts the distal tip of guide needle 202 at a first insertion site. The first insertion site, shown in FIGS. 4A and 4B, may be located lateral to the midline of the target vertebrae, and proximal to the cranial edge of the transverse process of the target vertebrae, just lateral to the base of the superior articular process. The clinician inserts guide needle 202 within the patient body at the first insertion site, e.g., directly or through a previously made incision, such that the longitudinal axis of guide needle 202 is approximately perpendicular, e.g., within ±10°, to the plane of a target anchor site, e.g., muscle such as the intertransversarii ITV of the target vertebrae. The clinician inserts the distal tip of guide needle 202 to a predetermined depth in proximity to the target implantation location. The clinician may insert the distal tip of guide needle 202 to a depth determined based on anatomical structures observed via lateral images and/or detected resistance. For example, to ensure accuracy for proper positioning of guide needle 202 visualization techniques such as x-ray, fluoroscopy, acoustic, anatomic, or CT guidance, may be used so the clinician may monitor guide needle 202 periodically via lateral and/or anterior/posterior images as guide needle 202 is advanced to the target implantation location. For example, from a lateral image, a clinician may understand that guide needle 202 is in the proper position when the distal tip of guide needle 202 is visible at an edge of an outline of the neural foramen of the target vertebrae.

Figure 4C:
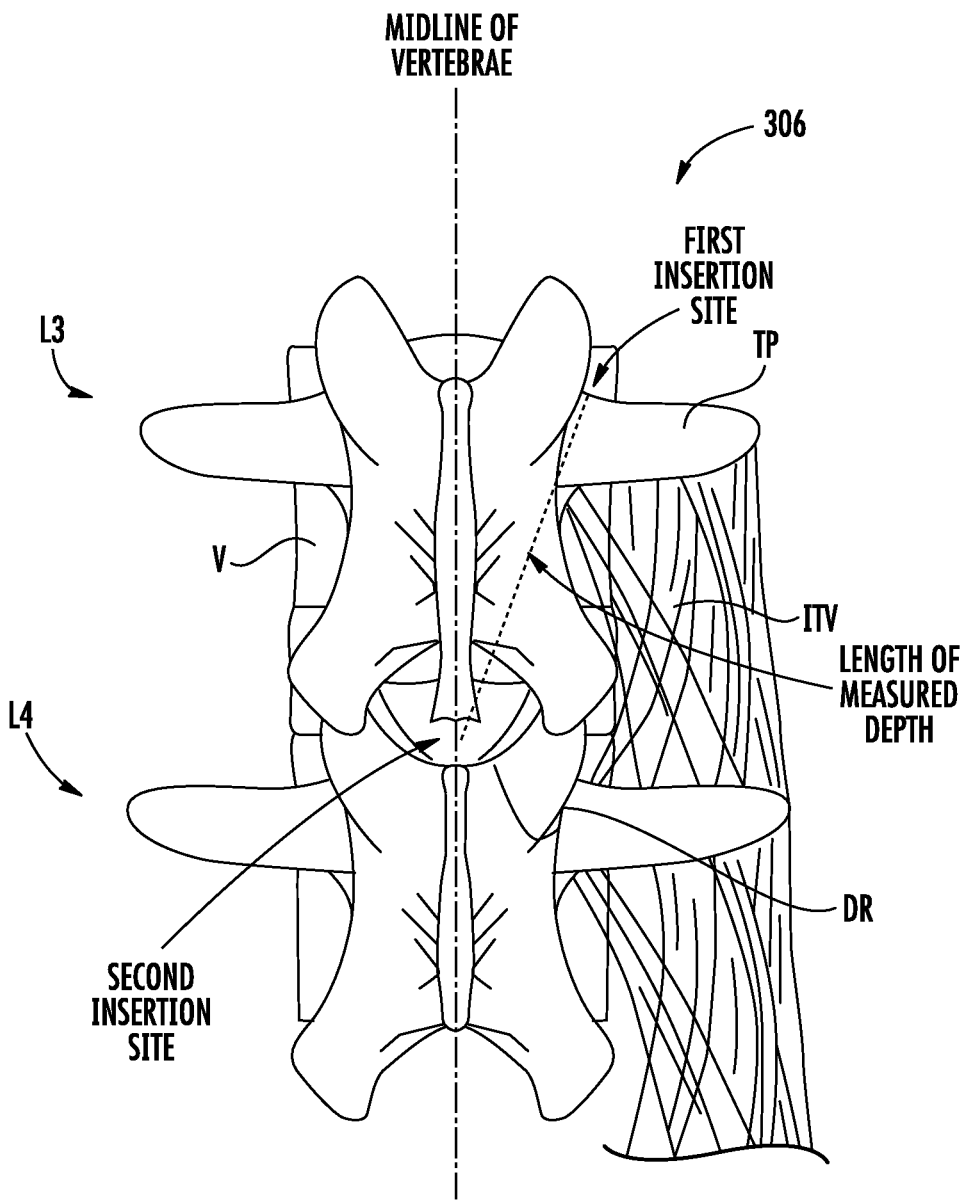

Referring back to FIG. 3 and now to FIG. 4C, step 306 is described. At 306, the clinician locates a second delivery needle insertion site. The second insertion site may be located along the midline of the target vertebrae and may be based on the depth attained by guide needle 202 in step 304. For example, the clinician may measure the depth attained by guide needle 202. The clinician may then locate the second insertion site such that the second insertion site is along the midline of the target vertebrae and at a distance from the first insertion site that is approximately equal to the depth attained by guide needle 202 in step 304. Preferably, the second insertion site is location anterior to the spinous process of the L4 vertebrae of the patient body.

Figure 4D:
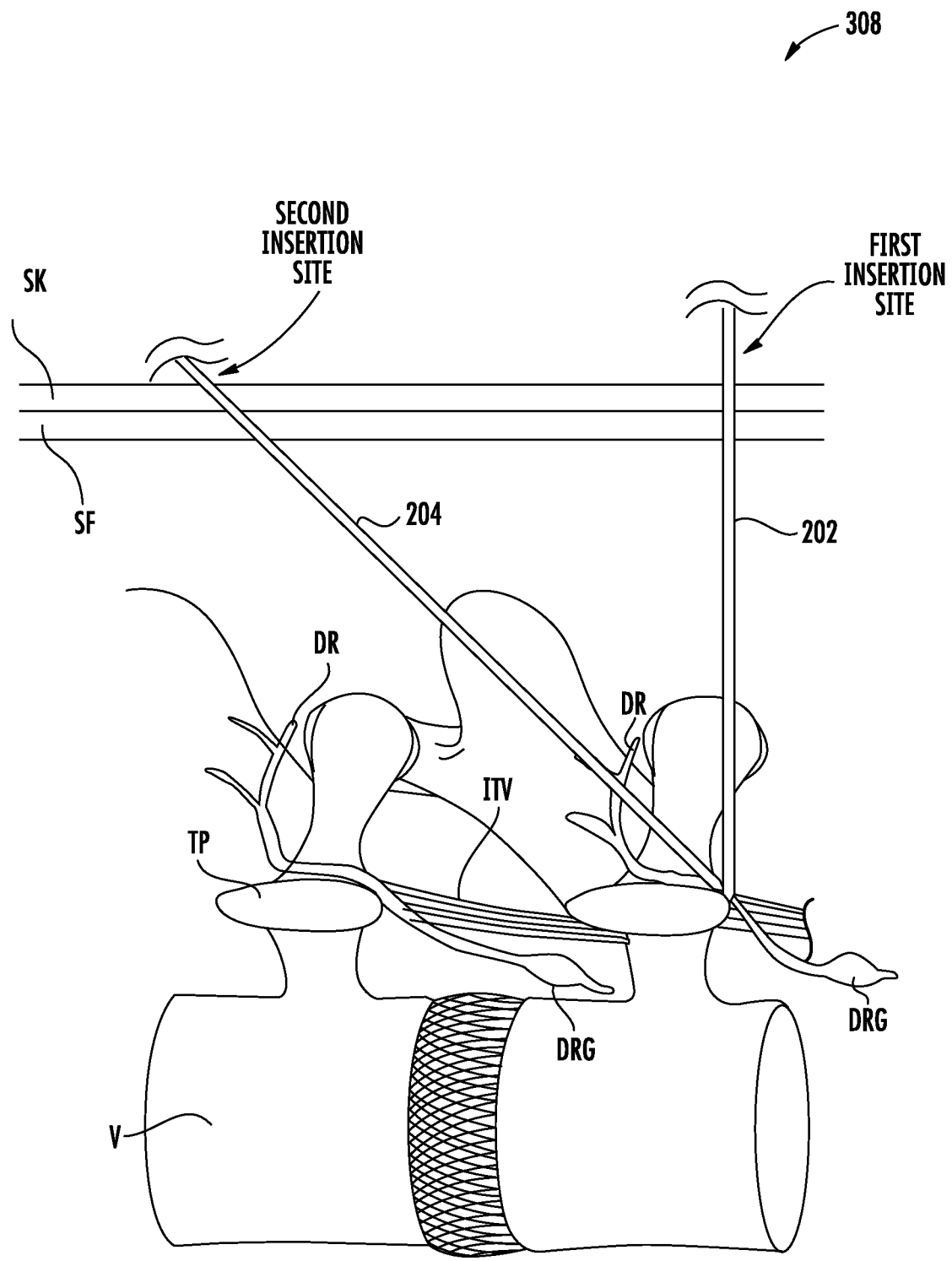

Referring back to FIG. 3 and now to FIG. 4D, step 308 is described. At 308, the clinician inserts the distal tip of delivery needle 204 at the second insertion site, e.g., directly or through a previously made incision. The distal tip of delivery needle 204 is inserted toward the distal tip of guide needle 202 such that the longitudinal axis of delivery needle 204 is angled relative to the longitudinal axis of guide needle 202. Preferably, the longitudinal axis of delivery needle 204 is angled relative to the longitudinal axis of guide needle 202 approximately 45 degrees, e.g., within ±10°. Accordingly, the longitudinal axis of delivery needle 204 is angled relative to the plane of the intertransversarii ITV approximately 45 degrees. The insertion method of delivery needle 204 by the clinician provides a medial-to-lateral trajectory from the second insertion site to the target implantation location such that the crisscross environment of the superficial and deep thoracolumbar fascia is avoided, and delivery needle 204 crosses the posterior thoracolumbar fascia at a point of minimal relative motion.

Preferably, delivery needle 204 is inserted with a consistent trajectory, such that the clinician may restart step 308 if necessary to avoid misalignment of the distal tip of delivery needle 204 to the distal tip of guide needle 202. Preferably, delivery needle 204 is advanced approximately 3-5 mm beyond the distal tip of guide needle 202, thereby penetrating the intertransversarii ITV of the target vertebrae. To ensure accuracy for proper positioning of delivery needle 204, using visualization techniques such as x-ray, fluoroscopy, acoustic, anatomic, or CT guidance, the clinician may monitor delivery needle 204 periodically via lateral and/or anterior/posterior images as delivery needle 204 is advanced to the target implantation location. For example, from a lateral image, a clinician may understand that delivery needle 204 is in the proper position when the distal tip of delivery needle 204 is visible at an edge of an outline of the neural foramen of the target vertebrae. In one embodiment, guide needle 202 may be removed from the patient body after delivery needle 204 is in the proper position.

Figure 4E:
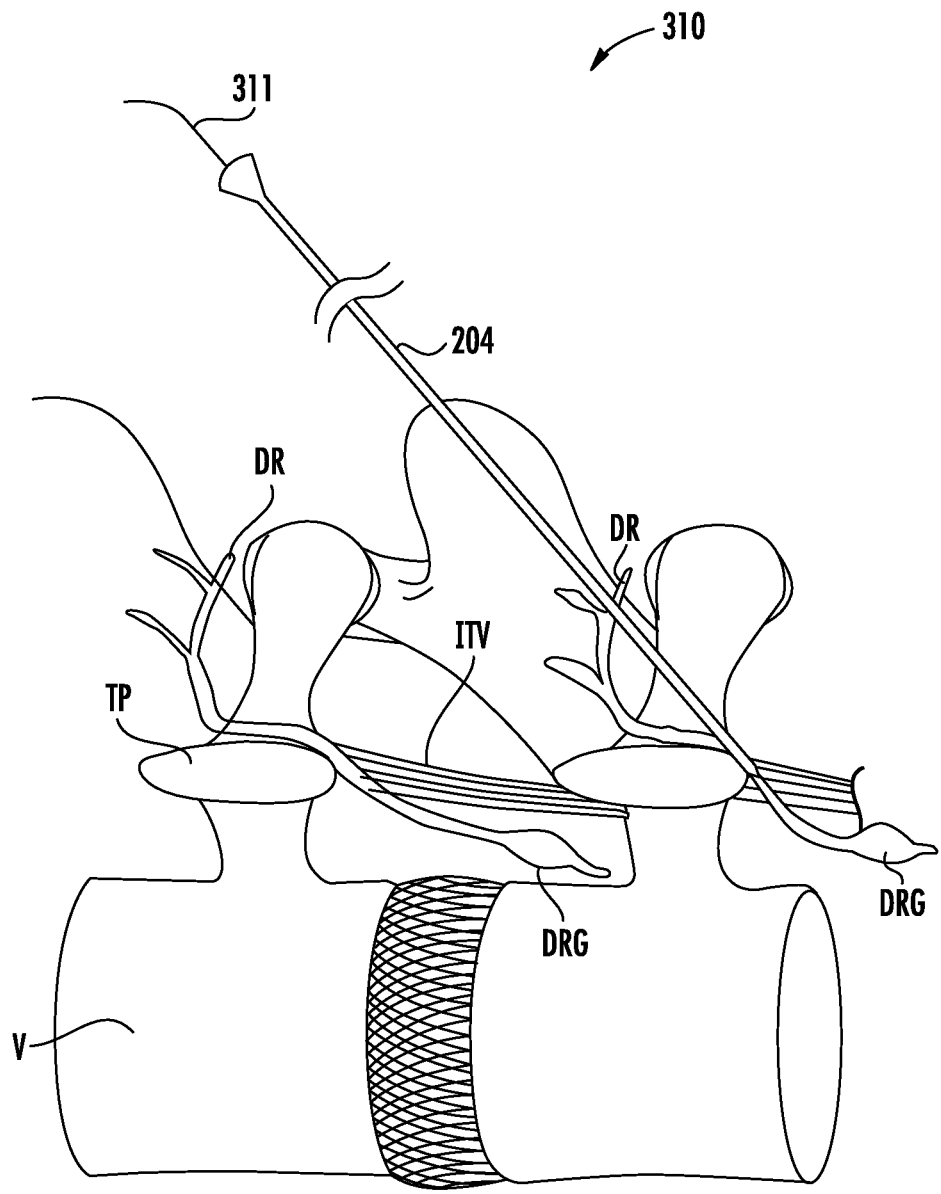

Referring back to FIG. 3 and now to FIG. 4E, step 310 is described. At 310, the clinician advances guidewire 311 through the lumen of delivery needle 204. Preferably, guidewire 311 exits the lumen of delivery needle 204 at the distal end of delivery needle 204 in a straight orientation. To ensure accuracy for proper positioning of guidewire 311, using fluoroscopy, acoustic, anatomic, or CT guidance, the clinician may monitor guidewire 311 periodically via lateral and/or anterior/posterior images as guidewire 311 exits the lumen of delivery needle 204 at the distal end of delivery needle 204.

In the event that guidewire 311 exits the lumen of delivery needle 204 at the distal end of delivery needle 204 such that guidewire 311 deflects cranially due to muscle tissue in proximity to the target implantation location, the clinician may remove guidewire 311 and reattempt step 310. In one embodiment, the clinician may remove both guidewire 311 and delivery needle 204, and reattempt both steps 308 and 310.

Figure 4F:
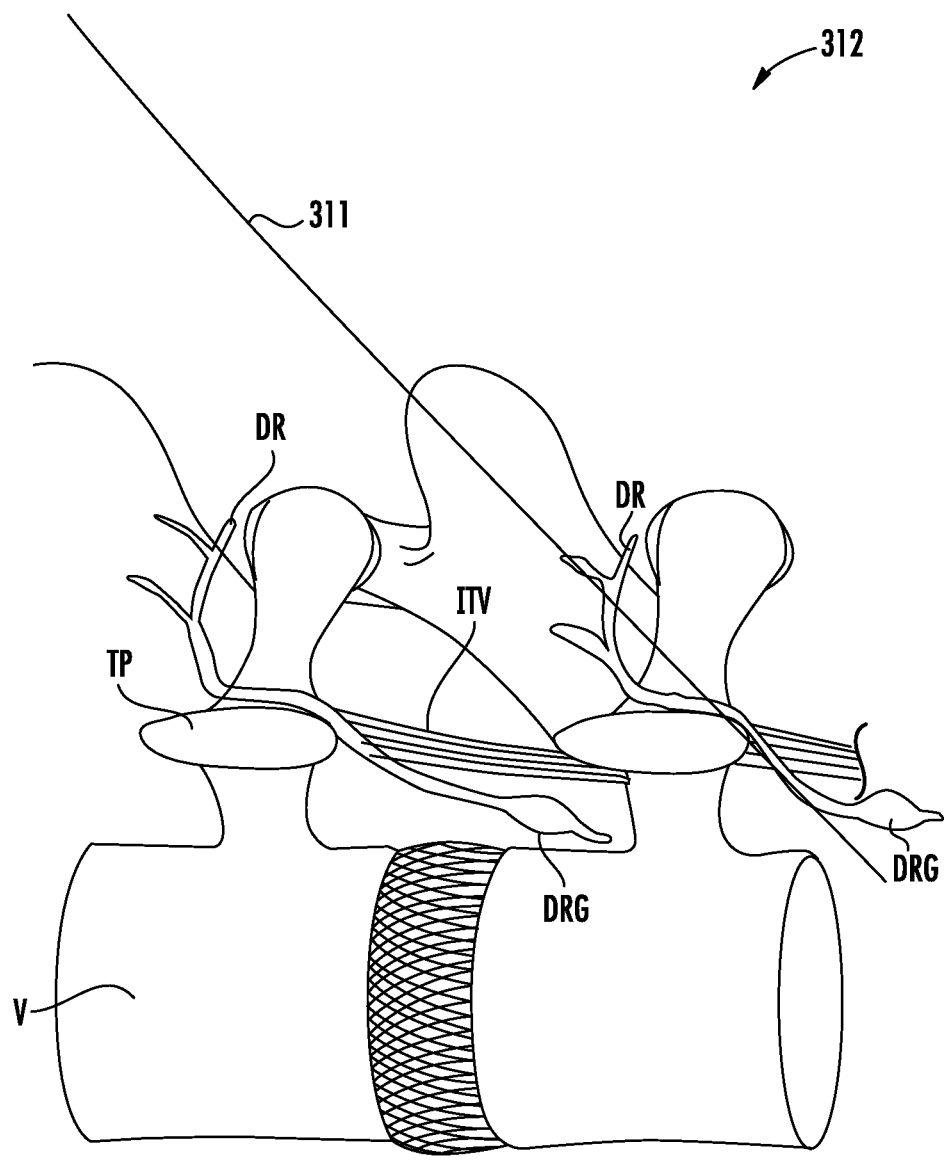

Referring back to FIG. 3 and now to FIG. 4F, step 312 is described. At 312, the clinician removes delivery needle 204 from the patient body, leaving behind guidewire 311.

Figure 4G:
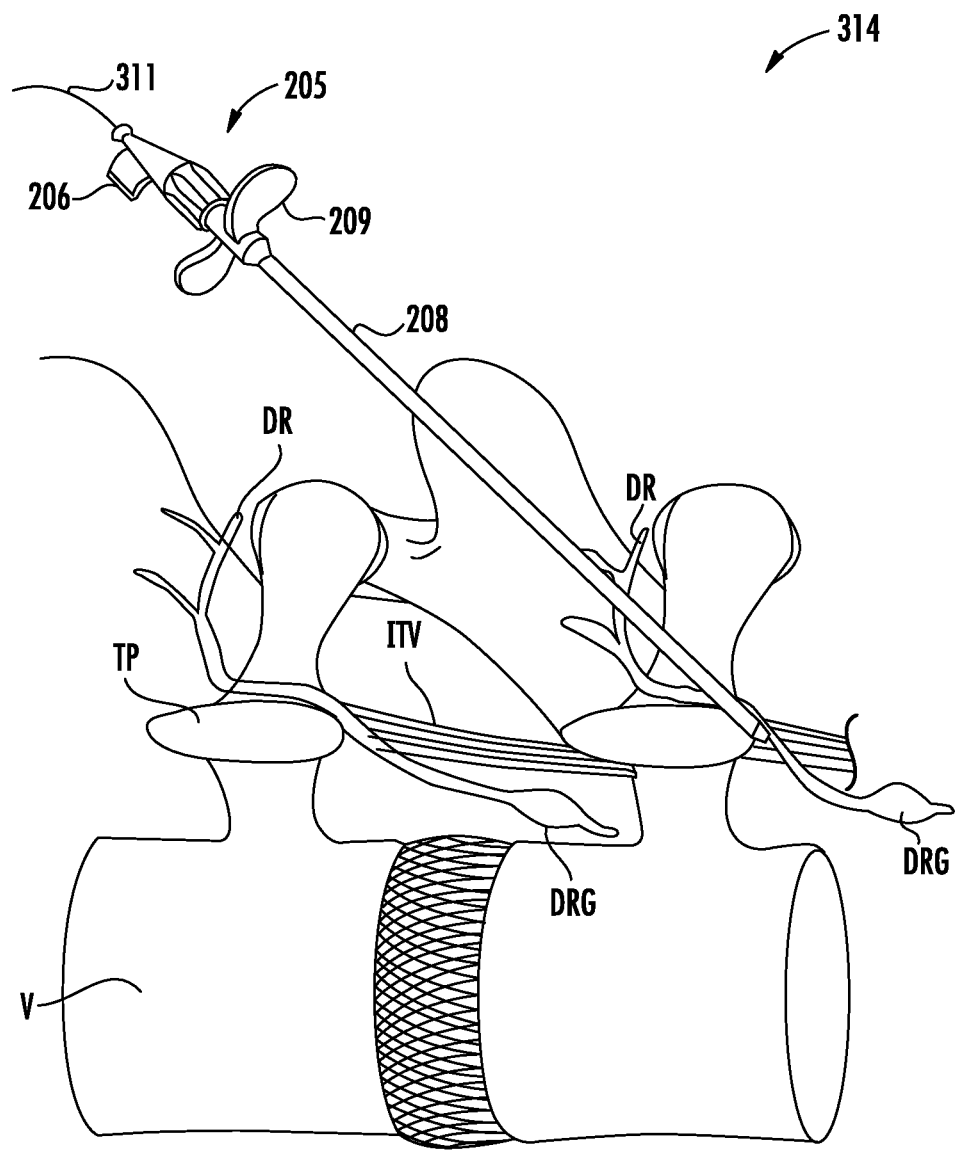

Referring back to FIG. 3 and now to FIG. 4G, step 314 is described. At 314, the clinician advances introducer assembly 205 over guidewire 311. The clinician may advance the distal tip of introducer assembly 205 through the intertransversarii ITV of the target vertebrae. To ensure accuracy for proper positioning of introducer assembly 205, using fluoroscopy, acoustic, anatomic, or CT guidance, the clinician may monitor introducer assembly 205 periodically via lateral and/or anterior/posterior images as introducer assembly 205 is advanced over guidewire 311 to the target implantation location. For example, from a lateral image, a clinician may understand that introducer assembly 205 is in the proper position when the distal tip of introducer assembly 205 is visible at an edge of an outline of the neural foramen of the target vertebrae. In addition, the clinician may use handle 209 of introducer sheath 208 to ensure advancement of introducer assembly 205 follows the same trajectory as delivery needle 204 over guidewire 311. In the event that introducer assembly 205 is not positioned within the plane of the intertransversarii, the clinician may remove introducer assembly 205 and reattempt step 314.

In one embodiment, introducer assembly 205 is advanced over guidewire 311 with dilator 206 disposed within introducer sheath 208. In this embodiment, introducer assembly 205 is advanced over guidewire 311 by receiving guidewire 311 through the lumen of dilator 206. Further in this embodiment, the clinician may remove dilator 206 from the lumen of introducer sheath 208 after the clinician removes guidewire 311 from the lumen of introducer assembly 205 as described in further detail below. For example, the clinician may rotate dilator 206 in a direction, e.g., counter-clockwise, to disengage it from the coupling portion of introducer sheath 208. In addition, the clinician may maintain slight forward pressure on introducer sheath 208 while removing dilator 206 from the lumen of introducer sheath 208.

Figure 4H:
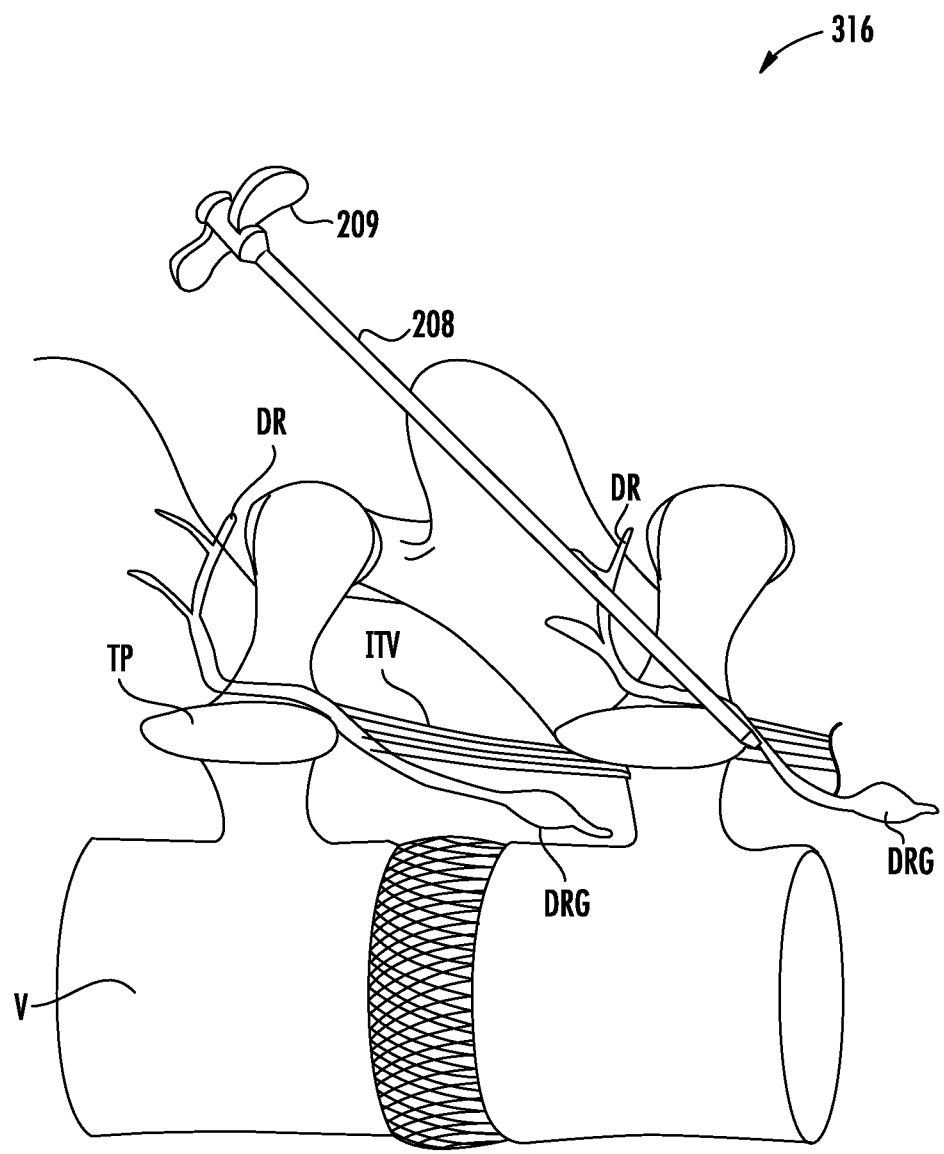

Referring back to FIG. 3 and now to FIG. 4H, step 316 is described. At 316, the clinician removes guidewire 311 from the lumen of introducer assembly 205, while maintaining the position of introducer assembly 205 at the target implantation location, e.g., within the plane of the intertransversarii ITV.

Figure 4I:
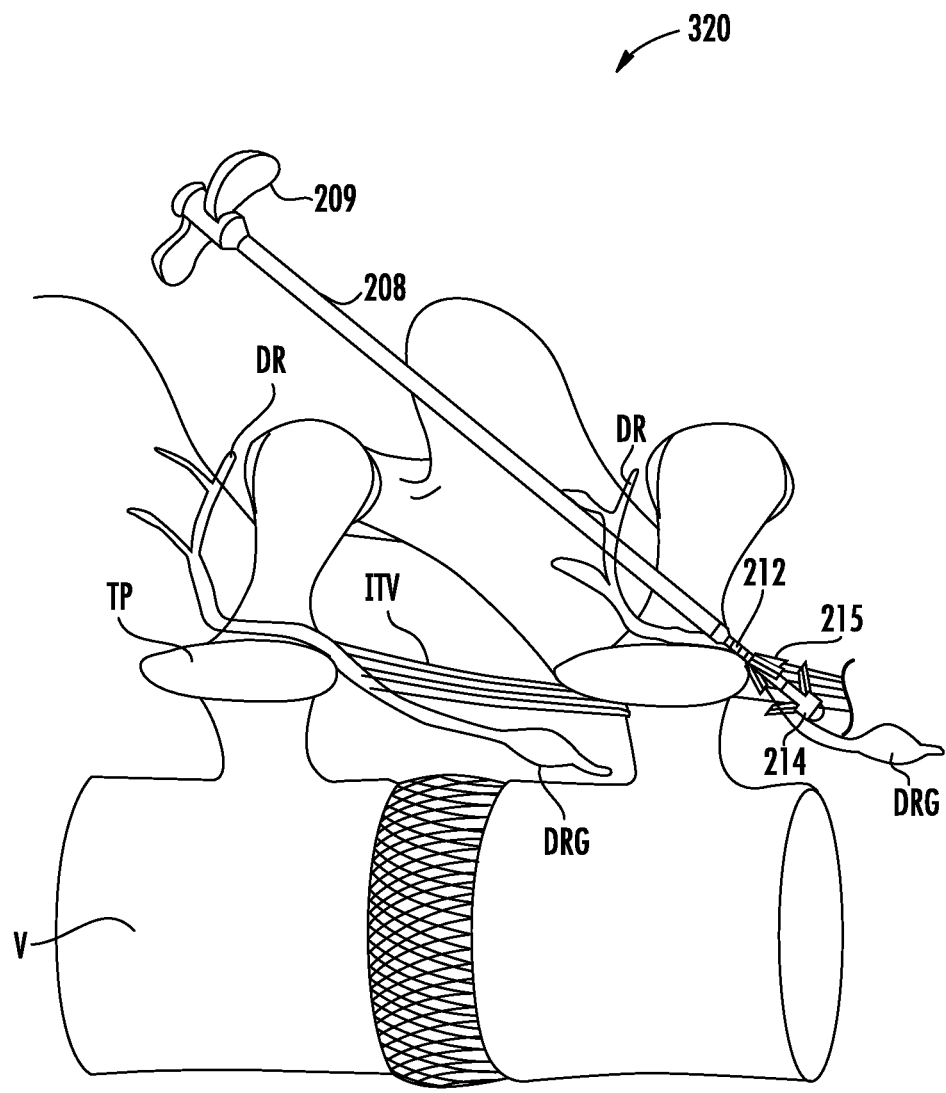

Referring back to FIG. 3 and now to FIG. 4I, steps 318 and 320 are described. At 318, the clinician advances electrode lead 212 through the lumen of introducer sheath 208. The clinician may advance electrode lead 212 until the distal end of electrode lead 212 is slightly proximal or distal to the distal tip of introducer sheath 208, such that the distal end of electrode lead 212 is in proximity to the target implantation location, e.g., in or adjacent to tissue associated with control of the lumbar spine. For example, the one or more electrodes may be implanted in or adjacent to nervous tissue associated with a target muscle(s). The one or more electrodes may be implanted in or adjacent to the dorsal ramus DR nerve, or fascicles thereof, innervating the multifidus muscle. In such embodiments, the one or more electrodes are configured to emit electrical energy to stimulate the dorsal ramus DR nerve, or fascicles thereof, to cause the multifidus to contract to thereby rehabilitate the multifidus and increase stability of the lumbar spine to reduce back pain. The one or more electrodes also may be configured to stimulate other nervous tissue such as the dorsal root ganglion DRG.

In one embodiment, a stylet is inserted within the stylet lumen of electrode lead 212 to provide additional stiffness to electrode lead 212 to ease passage of electrode lead 212 through introducer sheath 208. Electrode lead 212 with the stylet disposed therein then is advanced through the lumen of introducer sheath 208.

At 320, introducer assembly 205 is moved proximally off electrode lead 212, e.g., using handle 209 of introducer sheath 208, while maintaining the position of electrode lead 212 at the target implantation location, as shown in FIG. 4I. Fixation elements 214 and 215 of electrode lead 212 individually transition from a collapsed state within introducer assembly 205 to an expanded state as introducer assembly 205 passes over the respective fixation element. Fixation elements 214 and 215 sandwich an anchor site, e.g., muscle such as the intertransversarii ITV, therebetween without damaging the anchor site in the expanded state to fix electrode lead 212 at the target implantation location. For example, one of the fixation elements may be exposed from introducer sheath 208 and expand from a delivery state to a deployed state anterior to the intertransversarii IVT, while another one of the fixation elements may be exposed from introducer sheath 208 and expand from a delivery state to a deployed state posterior to the intertransversarii ITV. An impedance test may be conducted to determine that the fixation elements were properly deployed as described in U.S. Pat. No. 9,186,501 to Rawat.

To confirm that electrode lead 212 is properly positioned at the target implantation location such that electrode lead 212 is sufficiently anchored to the anchor site, the clinician may perform a push-pull test. The push-pull test may include gently pulling electrode lead 212 proximally until a predetermined resistance is felt. If fixation elements 214 and 215 successfully are in the deployed state, electrode lead 212 will experience approximately 2-3 mm of movement during the push-pull test administered by the clinician. In an embodiment comprising utilizing a stylet, the clinician may remove the stylet after determining that fixation elements 214 and 215 have successfully deployed and electrode lead 212 is properly anchored to the anchor site, prior to completely retracting introducer sheath 208.

In one embodiment, electrodes of electrode lead 212 are positioned to stimulate the medial branch of the dorsal ramus DR nerve, or fascicles thereof, that exits between the L2 and L3 lumbar segments and passes over the transverse process of the L3 vertebra, thereby eliciting contraction of fascicles of the lumbar multifidus at the L3, L4, L5 and S1 segments and in some patients also at the L2 segment.

In another embodiment, the electrodes are positioned to stimulate a peripheral nerve where the nerve enters skeletal muscle, which may be one or more of the multifidus, transverse abdominus, quadratus lumborum, psoas major, internus abdominus, obliquus externus abdominus, and erector spinae muscles. Such stimulation may induce contraction of the muscle to restore neural control and rehabilitate the muscle, thereby improving muscle function of local segmental muscles of the lumbar spine, improving lumbar spine stability, and reducing back pain.

Figure 4J:
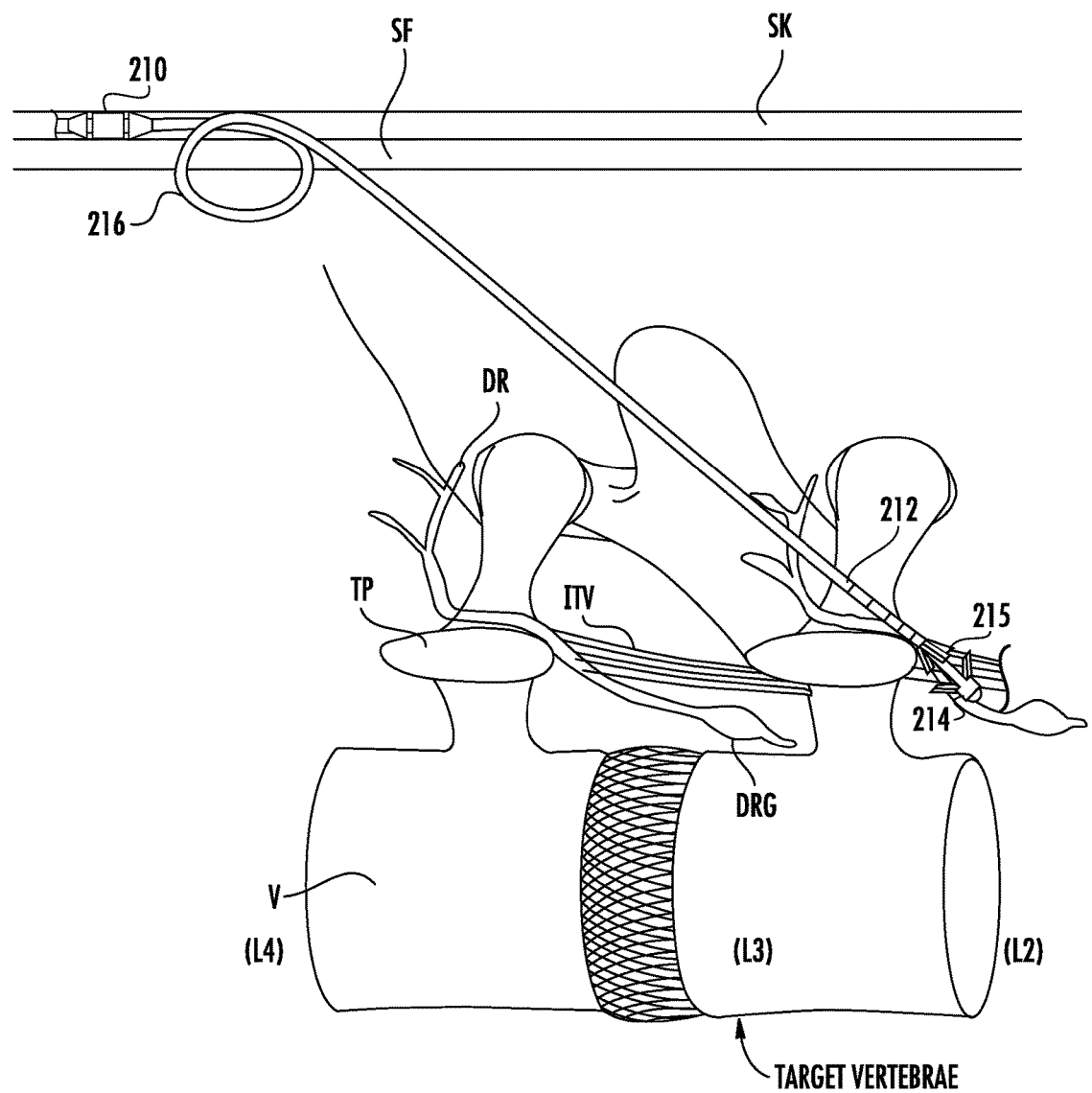

Referring now to FIG. 4J, the clinician may place suture sleeve 210 over the proximal end of electrode lead 212 and moved distally. When suture sleeve 210 is positioned adjacent to the superficial fascia SF beneath skin SK, sutures are sewn into the first and second grooves of suture sleeve 210 so as to secure suture sleeve 210 to the superficial fascia SF.

In one embodiment, as shown in FIG. 4J, electrode lead 212 may include strain relief portion 216 as described below. Strain relief portion 216 is configured to reduce lead dislodgement and/or fracture after implantation due to, for example, the lack of suitable anchor sites for the electrode leads, the torsional and/or bending stresses imposed on the electrode leads by movement of the surrounding muscles. As described below, strain relief portion 216 may take on a variety of structures that are designed to reduce the strain on electrode lead 212 and the fixation elements, thereby reducing the risk of lead dislodgement, fatigue fracture, and injury to the nervous tissue through which electrode lead 212 passes. In the embodiment shown in FIG. 4J, strain relief portion 216 comprises a loop. Preferably, the loop comprises a diameter of at least 2 cm. In an alternative embodiment, strain relief portion 216 comprises a "C" shape. Other strain relief structures designed to reduce the strain on electrode lead 212 and fixation elements 214 and 215 of the present disclosure are described in U.S. Patent Application Pub. No. 2014/0350653 to Shiroff, assigned to the assignee of the present disclosure, the entire contents of which are incorporated herein by reference. Strain relief portion 216 permits extension of electrode lead 212 between the proximal end and the distal end of electrode lead 212 without imposing excessive loads on the fixation elements 214 and 215 that could result in axial displacement of the electrodes.

Finally, the proximal end of the lead may be subcutaneously tunneled to the IPG using a tunneler system and coupled to the IPG such that the IPG is implanted in a suitable location, e.g., the lower back of the patient, and the electrode lead is fully implanted.

Figure 5B:
FIGS. 5A and 5B illustrate multiple electrode leads implanted via a midline insertion in accordance with the principles of the present disclosure from an anterior/posterior view in FIG. 5A and a lateral view in FIG. 5B.
Figure 5A:

Referring now to FIGS. 5A and 5B, multiple electrode leads may be implanted in accordance with the principles of the present disclosure. The illustrated electrode leads may be structurally similar to electrode lead 212 of FIG. 2 described above, and may each contain a plurality of electrodes disposed at their respective distal ends. The plurality of electrodes are configured to be implanted in or adjacent to tissue at the opposing side of the spine, such as nervous tissue, muscle, ligament, and/or joint capsule. As illustrated in FIGS. 5A and 5B, the electrode leads may be anchored at different anchor sites. For example, after implanting a first electrode lead as described in FIGS. 4A through 4J, the implantation method may be repeated on the opposing side of the spine to implant a second electrode lead. As a result, one electrode lead may be anchored such that the plurality of electrodes disposed thereon are in or adjacent to the dorsal root ganglion and/or the medial branch of the dorsal ramus nerve, or fascicles thereof, that innervates the multifidus muscle located on one side of the target vertebrae, while the other electrode lead may simultaneously be anchored such that the plurality of electrodes disposed thereon are in or adjacent to the dorsal root ganglion and/or the medial branch of the dorsal ramus nerve, or fascicles thereof, that innervates the multifidus muscle located on the opposite side of the target vertebrae.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A method for implanting a device for restoring muscle function to a lumbar spine, the method comprising:
   selecting a guide needle having a longitudinal axis and a distal tip;
   selecting a lead having a distal region including one or more electrodes;
   locating a target vertebrae of the lumbar spine;
   inserting the distal tip of the guide needle percutaneously at a first insertion site a lateral distance from a midline of the target vertebrae to a depth;
   measuring the depth attained by the distal tip of the guide needle;
   locating a second insertion site along the midline of the target vertebrae based on the depth, the second insertion site located a distance from the first insertion site approximately equal to the depth; and
   implanting the lead at the second insertion site with the distal region angled relative to the longitudinal axis of the guide needle, so that the lead traverses naturally occurring fascicle planes and the one or more electrodes are disposed in or adjacent to a tissue associated with control of the lumbar spine.

2. The method of claim 1, wherein locating the target vertebrae comprises locating an L3 vertebrae.

3. The method of claim 1, wherein the first insertion site is located at a cranial edge of a transverse process of the target vertebrae and proximately lateral to a base of a superior articular process of the target vertebrae.

4. The method of claim 1, wherein the second insertion site is located above an L4 spinous process.

5. The method of claim 1, wherein the one or more electrodes are disposed in or adjacent to a dorsal ramus nerve or fascicles thereof.

6. The method of claim 1, further comprising implanting an implantable pulse generator configured to be coupled to the lead.

7. The method of claim 1, wherein implanting the lead at the second insertion site comprises:
   selecting a delivery needle having a distal tip, a lumen and a longitudinal axis;
   inserting the distal tip of the delivery needle percutaneously at the second insertion site such that the longitudinal axis of the delivery needle is angled relative to the longitudinal axis of the guide needle;
   advancing a guidewire through the lumen of the delivery needle;
   removing the delivery needle;
   advancing an introducer assembly over the guidewire;
   removing the guidewire;
   advancing the lead through the introducer assembly so that the one or more electrodes are disposed in or adjacent to the tissue associated with control of the lumbar spine; and
   retracting the introducer assembly.

8. The method of claim 7, wherein the longitudinal axis of the delivery needle is approximately angled 45 degrees relative to the longitudinal axis of the guide needle.

9. The method of claim 7, wherein inserting the distal tip of the delivery needle further comprises visualizing the distal tip of the delivery needle within an outline of a neural foramen of the target vertebrae.

10. The method of claim 7, wherein inserting the distal tip of the delivery needle further comprises advancing the distal tip of the delivery needle approximately 3-5 mm beyond the distal tip of the guide needle, thereby penetrating an intertransversarii.

11. The method of claim 7, further comprising removing the guide needle after inserting the distal tip of the delivery needle percutaneously at the second insertion site.

12. The method of claim 7, wherein advancing the introducer assembly over the guidewire further comprises visualizing a distal tip of the introducer assembly within an outline of a neural foramen of the target vertebrae to confirm placement of the introducer assembly within a plane of an intertransversarii.

13. The method of claim 7, wherein the lead comprises one or more fixation elements disposed in proximity to at least one of the one or more electrodes, the one or more fixation elements configured to transition from a delivery state, wherein the one or more fixation elements are positioned adjacent to the at least one of the one or more electrodes, to a deployed state, wherein the one or more fixation elements are spaced apart from the at least one of the one or more electrodes and positioned to anchor the lead to an anchor site,
   wherein retracting the introducer assembly causes the one or more fixation elements to transition from the delivery state to the deployed state.

14. The method of claim 7, wherein the introducer assembly comprises a dilator having a lumen extending therethrough configured to receive the guidewire, and an introducer sheath having a lumen extending therethrough configured to receive the dilator, the method further comprising removing the dilator prior to advancing the lead through the introducer assembly.

15. A method for implanting a device for restoring muscle function to a lumbar spine, the method comprising:

selecting a guide needle having a longitudinal axis and a distal tip;
selecting a lead having a distal region including one or more electrodes;
locating a target vertebrae of the lumbar spine;
inserting the distal tip of the guide needle percutaneously at a first insertion site a lateral distance from a midline of the target vertebrae to a depth, the first insertion site located at a superior articular process of the target vertebrae;
locating a second insertion site along the midline of the target vertebrae based on the depth; and
implanting the lead at the second insertion site with the distal region angled relative to the longitudinal axis of the guide needle, so that the lead traverses naturally occurring fascicle planes and the one or more electrodes are disposed in or adjacent to a tissue associated with control of the lumbar spine.

16. The method of claim 15, wherein locating the target vertebrae comprises locating an L3 vertebrae.

17. The method of claim 15, further comprising measuring the depth attained by the distal tip of the guide needle, the second insertion site located a distance from the first insertion site approximately equal to the depth.

18. The method of claim 15, wherein the second insertion site is located above an L4 spinous process.

19. The method of claim 15, wherein the one or more electrodes are disposed in or adjacent to a dorsal ramus nerve or fascicles thereof.

20. The method of claim 15, further comprising implanting an implantable pulse generator configured to be coupled to the lead.

21. The method of claim 15, wherein implanting the lead at the second insertion site comprises:
selecting a delivery needle having a distal tip, a lumen and a longitudinal axis;
inserting the distal tip of the delivery needle percutaneously at the second insertion site such that the longitudinal axis of the delivery needle is angled relative to the longitudinal axis of the guide needle;
advancing a guidewire through the lumen of the delivery needle;
removing the delivery needle;
advancing an introducer assembly over the guidewire;
removing the guidewire;
advancing the lead through the introducer assembly so that the one or more electrodes are disposed in or adjacent to the tissue associated with control of the lumbar spine; and
retracting the introducer assembly.

22. The method of claim 21, wherein the longitudinal axis of the delivery needle is approximately angled 45 degrees relative to the longitudinal axis of the guide needle.

23. The method of claim 21, wherein inserting the distal tip of the delivery needle further comprises visualizing the distal tip of the delivery needle within an outline of a neural foramen of the target vertebrae.

24. The method of claim 21, Wherein inserting the distal tip of the delivery needle further comprises advancing the distal tip of the delivery needle approximately 3-5 mm beyond the distal tip of the guide needle, thereby penetrating an intertransversarii.

25. The method of claim 21, further comprising removing the guide needle after inserting the distal tip of the delivery needle percutaneously at the second insertion site.

26. The method of claim 21, wherein advancing the introducer assembly over the guidewire further comprises visualizing a distal tip of the introducer assembly within an outline of a neural foramen of the target vertebrae to confirm placement of the introducer assembly within a plane of an intertransversarii.

27. The method of claim 21, wherein the lead comprises one or more fixation elements disposed in proximity to at least one of the one or more electrodes, the one or more fixation elements configured to transition from a delivery state, wherein the one or more fixation elements are positioned adjacent to the at least one of the one or more electrodes, to a deployed state, wherein the one or more fixation elements are spaced apart from the at least one of the one or more electrodes and positioned to anchor the lead to an anchor site,
wherein retracting the introducer assembly causes the one or more fixation elements to transition from the delivery state to the deployed state.

28. The method of claim 21, wherein the introducer assembly comprises a dilator having a lumen extending therethrough configured to receive the guidewire, and an introducer sheath having a lumen extending therethrough configured to receive the dilator, the method further comprising removing the dilator prior to advancing the lead through the introducer assembly.

29. A method for implanting a device for restoring muscle function to a lumbar spine, the method comprising:
selecting a guide needle having a longitudinal axis and a distal tip;
selecting a lead having a distal region including one or more electrodes;
locating a target vertebrae of the lumbar spine;
inserting the distal tip of the guide needle percutaneously at a first insertion site a lateral distance from a midline of the target vertebrae to a depth;
locating a second insertion site along the midline of the target vertebrae based on the depth; and
implanting the lead at the second insertion site with the distal region angled relative to the longitudinal axis of the guide needle, so that the lead traverses naturally occurring fascicle planes and the one or more electrodes are disposed in or adjacent to a tissue associated with control of the lumbar spine,
wherein implanting the lead at the second insertion site comprises:
selecting a delivery needle having a distal tip, a lumen and a longitudinal axis;
inserting the distal tip of the delivery needle percutaneously at the second insertion site such that the longitudinal axis of the delivery needle is angled approximately 45 degrees relative to the longitudinal axis of the guide needle;
advancing a guidewire through the lumen of the delivery needle;
removing the delivery needle;
advancing an introducer assembly over the guidewire;
removing the guidewire;
advancing the lead through the introducer assembly so that the one or more electrodes are disposed in or adjacent to the tissue associated with control of the lumbar spine; and
retracting the introducer assembly.

30. A method for implanting a device for restoring muscle function to a lumbar spine, the method comprising:
selecting a guide needle having a longitudinal axis and a distal tip;
selecting a lead having a distal region including one or more electrodes;

locating a target vertebrae of the lumbar spine;
inserting the distal tip of the guide needle percutaneously at a first insertion site a lateral distance from a midline of the target vertebrae to a depth;
locating a second insertion site along the midline of the target vertebrae based on the depth; and
implanting the lead at the second insertion site with the distal region angled relative to the longitudinal axis of the guide needle, so that the lead traverses naturally occurring fascicle planes and the one or more electrodes are disposed in or adjacent to a tissue associated with control of the lumbar spine,
wherein implanting the lead at the second insertion site comprises:
    selecting a delivery needle having a distal tip, a lumen and a longitudinal axis;
    inserting the distal tip of the delivery needle percutaneously at the second insertion site such that the longitudinal axis of the delivery needle is angled relative to the longitudinal axis of the guide needle, and advancing the distal tip of the delivery needle approximately 3-5 mm beyond the distal tip of the guide needle, thereby penetrating an intertransversarii;
advancing a guidewire through the lumen of the delivery needle;
removing the delivery needle;
advancing an introducer assembly over the guidewire;
removing the guidewire;
advancing the lead through the introducer assembly so that the one or more electrodes are disposed in or adjacent to the tissue associated with control of the lumbar spine; and
retracting the introducer assembly.

\* \* \* \* \*